United States Patent [19]

Harnden et al.

[11] Patent Number: 5,247,085
[45] Date of Patent: Sep. 21, 1993

[54] ANTIVIRAL PURINE COMPOUNDS

[75] Inventors: Michael R. Harnden; David M. Duckworth, both of Epsom, England

[73] Assignee: Beecham Group p.l.c., Brentford, England

[21] Appl. No.: 892,601

[22] Filed: May 29, 1992

Related U.S. Application Data

[63] Continuation of Ser. No. 530,736, May 19, 1990, abandoned, which is a continuation-in-part of Ser. No. 276,868, Nov. 28, 1988, abandoned, and a continuation-in-part of Ser. No. 387,068, Jul. 28, 1989, Pat. No. 5,055,458, and a continuation-in-part of Ser. No. 528,575, May 23, 1990, Pat. No. 5,108,994.

[30] Foreign Application Priority Data

Nov. 30, 1987 [GB] United Kingdom ............... 8727988
May 16, 1988 [GB] United Kingdom ............... 8811575
May 30, 1989 [GB] United Kingdom ............... 8912348
May 30, 1989 [GB] United Kingdom ............... 8912349

[51] Int. Cl.$^5$ ............... C07F 9/6512; A61K 31/675; C07D 233/90
[52] U.S. Cl. ............... 544/244; 558/175; 548/112; 544/243
[58] Field of Search ............ 514/81, 86; 544/243, 544/244

[56] References Cited

U.S. PATENT DOCUMENTS 4,808,716  2/1989  Holy et al. ............... 544/244
4,910,307  3/1990  Wyatt ............... 544/276
5,055,458  10/1991  Bailey et al. ............... 514/81

FOREIGN PATENT DOCUMENTS 0206459  12/1986  European Pat. Off. .
0313289  4/1989  European Pat. Off. .
0319228  6/1989  European Pat. Off. ............... 544/244
0353955  2/1990  European Pat. Off. .
2085671  12/1971  France .

OTHER PUBLICATIONS

Ashton, J. Cellular Biochem. 16F Suppl., Mar. 1992, Abstract Q-503.
Perkins, J. Cellular Biochem. 16E, Suppl., Mar. 1992, Abstract Q548.
Hollingshed, Antiviral Research, Supp. I, Mar. 1992, p. 59, Abstract 30.
Ruprecht, Nature 323, pp. 467–469 (1986).
Prisbe, et al., J. Med. Chem., vol. 29(5), pp. 671–675 (May 1986).
Duke, et al., Antiviral Research, vol. 6, pp. 299–308 (1986).
Striecher, et al., Chemica Scripta, vol. 26, pp. 179–183 (1986).

Primary Examiner—Mark L. Berch
Attorney, Agent, or Firm—Hopgood, Calimafde, Kalil, Blaustein & Judlowe

[57] ABSTRACT

Compounds of formula (I), and pharmaceutically acceptable salts thereof

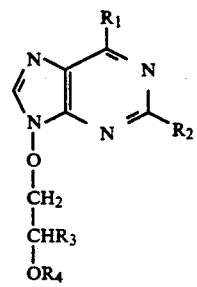

wherein
$R_1$ is hydroxy, amino, chloro or $OR_7$ wherein
$R_7$ is $C_{1-6}$ alkyl, phenyl or phenyl $C_{1-2}$ alkyl either of which phenyl moieties may be substituted by one or two substituents selected from halo, $C_{1-4}$ alkyl or $C_{1-4}$ alkoxy;
$R_2$ is amino or, when $R_1$ is hydroxy or amino, $R_2$ may also be hydrogen;
$R_3$ is hydrogen, hydroxymethyl or acyloxymethyl;
$R_4$ is a group of formula:

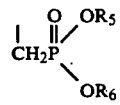

$R_5$ and $R_6$ are independently selected from hydrogen, $C_{1-6}$ alkyl and optionally substituted phenyl; or
$R_3$ and $R_4$ together are:

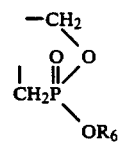

wherein
$R_6$ is as defined above;
having antiviral activity, to processes for their preparation and their use as pharmaceuticals.

8 Claims, No Drawings

ANTIVIRAL PURINE COMPOUNDS

This application is a continuation of Ser. No. 530,736 (filed May 19, 1990), abandoned, which in turn is a continuation-in-part of Ser. No. 276,868 (filed Nov. 28, 1988), abandoned, of Ser. No. 387,068 (filed Jul. 28, 1989), U.S. Pat. No. 5,055,458, and of Ser. No. 528,575 (filed May 19, 1990) U.S. Pat. No. 5,108,994.

The present invention relates to compounds having antiviral activity, to processes for their preparation and to their use as pharmaceuticals.

EP-A-242482 (Beecham Group p.l.c.) describes a group of guanine derivatives having a 9-hydroxyalkoxy substituent, and possessing antiviral activity.

A novel, structurally distinct class of compounds has now been discovered, these compounds also having antiviral activity.

Accordingly, the present invention provides a compound of formula (I), or a pharmaceutically acceptable salt thereof:

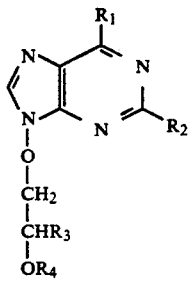

wherein $R_1$ is hydroxy, amino, chloro or $OR_7$ wherein $R_7$ is $C_{1-6}$ alkyl, phenyl or phenyl $C_{1-2}$ alkyl either of which phenyl moieties may be substituted by one or two substituents selected from halo, $C_{1-4}$ alkyl or $C_{1-4}$ alkoxy;

$R_2$ is amino or, when $R_1$ is hydroxy or amino, $R_2$ may also be hydrogen;

$R_3$ is hydrogen, hydroxymethyl or acyloxymethyl;

$R_4$ is a group of formula:

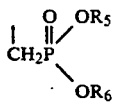

wherein $R_5$ and $R_6$ are independently selected from hydrogen, $C_{1-6}$ alkyl and optionally substituted phenyl; or $R_3$ and $R_4$ together are:

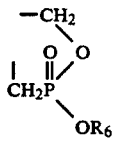

wherein $R_6$ is as defined above.

When $R_1$ is hydroxy and $R_2$ is amino, the compound of formula (I) is a guanine derivative;

When $R_1$ is amino and $R_2$ is hydrogen, the compound of formula (I) is an adenine derivative;

When $R_1$ is hydroxy and $R_2$ is hydrogen, the compound of formula (I) is a hypoxanthine derivative; and When $R_1$ and $R_2$ are both amino groups, the compound of formula (I) is a 2,6-diaminopurine derivative.

Often, the compound of formula (I) is a guanine or adenine derivative, preferably an adenine derivative.

Suitable examples of the acyl group in $R_3$ when acyloxymethyl, include carboxylic acyl, such as $C_{1-7}$ alkanoyl and benzoyl optionally substituted in the phenyl ring include acetyl, propionyl, butyryl, heptanoyl and hexanoyl.

Suitable examples of $R_5$ and $R_6$ include hydrogen, methyl, ethyl, n- and iso-propyl, n-, sec-, iso- and tert-butyl, and phenyl optionally substituted by one, two or three groups or atoms selected from halogen, such as fluoro, chloro, bromo, and $C_{1-4}$ alkyl or $C_{1-4}$ alkoxy wherein the alkyl moiety is selected from those listed for $R_5/R_6$ above.

Examples of $R_7$ include methyl, ethyl, n- and iso-propyl, phenyl and benzyl optionally substituted by one or two of methyl, ethyl, n- and iso-propyl, methoxy, ethoxy, n- and iso-propoxy, fluoro, chloro or bromo.

Examples of pharmaceutically acceptable salts of the compound of formula (I) are acid addition salts formed with a pharmaceutically acceptable acid such as hydrochloric acid, orthophosphoric acid and sulphuric acid. Pharmaceutically acceptable salts also include those formed with organic bases, preferably with amines, such as ethanolamines or diamines; and alkali metals, such as sodium and potassium.

As the compound of formula (I) contains a phosphonate group, suitable salts include metal salts, such as alkali metal salts, for example sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine.

It will be appreciated that some of the compounds of formula (I), especially those wherein $R_3$ is other than hydrogen, have an asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively, the individual isomers may be prepared by asymmetric synthesis using chiral intermediates.

The compounds of formula (I) including their alkali metal salts may form solvates such as hydrates and these are included wherever a compound of formula (I) or a salt thereof is herein referred to.

It will be appreciated that, when $R_1$ is hydroxy in formula (I) the compound exists in the predominant tautomeric form of structure (IA):

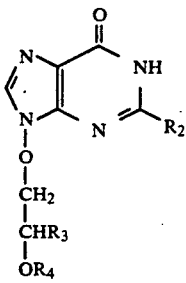

(IA)

The invention also provides a process for the preparation of a compound of formula (I), or a pharmaceuticallty acceptable salt thereof, which process comprises either i) imidazole ring closure of a compound of formula (II):

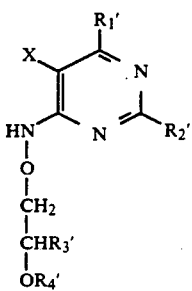

(II)

wherein X is a group capable of cyclising to form an imidazole ring, such as amino or an amino derivative, for example, formylamino; or ii) pyrimidine ring closure of a compound of formula (III):

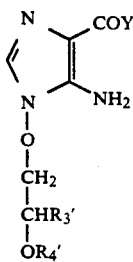

(III)

wherein Y is amino or $C_{1-6}$ alkoxy, with a condensing agent capable of cyclising to form a pyrimidine ring having a 2-$R_2'$ substituent, to give a compound of formula (I) wherein $R_1$ is hydroxy and $R_2$ is amino; or iii) condensing a compound of formula (IV):

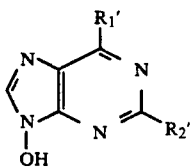

(IV)

with a side chain intermediate of formula (V):

$ZCH_2-CHR_3'OR_4'$ (V)

wherein Z is a leaving group;

and wherein, in formulae (II) to (V), $R_1'$, $R_2'$, $R_3'$, $R_4'$ are $R_1$, $R_2$, $R_3$ and $R_4$ respectively, or groups or atoms convertible thereto; and thereafter, when desired or necessary, converting $R_1'$, $R_2'$, $R_3'$ and/or $R_4'$, when other than $R_1$, $R_2$, $R_3$ and/or $R_4$ to $R_1$, $R_2$, $R_3$ and/or $R_4$ respectively, and/or converting $R_1'$, $R_2'$, $R_3'$ and/or $R_4'$ when $R_1$, $R_2$, $R_3$ and/or $R_4$, to other $R_1$, $R_2$, $R_3$ and/or $R_4$.

Process i) may be carried out, preferably when X is formyl, using a cyclisation condensing agent, such as diethoxymethyl acetate or triethyl orthoformate, or by fusion.

Process ii) is preferably carried out in accordance with the methods described in EP-A-242482, the subject matter of which is incorporated herein by reference.

Process iii) may be carried out with suitable values for Z including hydroxy and halo, such as chloro, bromo and iodo, preferably iodo; or other groups readily displaceable by nucleophiles, such as mesyloxy or tosyloxy. The reaction preferably takes place in an inert solvent, such as dimethylformamide at 0°–50° C., preferably ambient temperature. When Z is hydroxy, the reaction takes place in the presence of a dehydrating catalyst, such as diethyl azodicarboxylate in the presence of triphenylphosphine. When Z is halo, the reaction preferably takes place in the presence of a base, such as potassium carbonate.

Examples of conversions of variable groups are as follows:

$R_1'$—$R_1$ a) An $R_1$ hydroxy group may be converted to $R_1'$ is chloro, by chlorination using a reagent such as phosphorus oxychloride, preferably in the presence of tetraethylammonium chloride and dimethylaniline (as acid acceptor) in $CH_3CN$ at reflux temperatures, according to the method described by M. J. Robins and B. Ozanski Can. J. Chem, 59, 2601 (1981).

b) An $R_1'$ chloro group may be converted to $R_1$ is hydroxy by hydrolysis using aqueous mineral acid, such as hydrochloric acid, or more preferably, using an organic acid, such as formic acid at elevated temperature, suitably 70°–150° C., preferably around 100° C.

c) An $R_1'$ chloro group may be converted to $R_1$ is amino by treatment with ammonia in a lower alkanol, such as ethanol or methanol in an autoclave at 100° C. for a period of about 7 hours, or alternatively, by treatment with sodium azide in dimethylformamide (forming an $R_1$ is $N_3$ intermediate), followed by reduction with ammonium formate/palladium or charcoal, in methanol.

d) An $R_1'$ alkoxy group, such as methoxy, may be converted to $R_1$ hydroxy by the methods of D. R. Haines, J. Med. Chem. 1987, 30, 943 and K. K. Ogilvie and H. R. Hanna, Can. J. Chem. 1984, 62, 2702.

e) An $R_1'$ protected amino group, such as tritylamino, may be converted to amino, by treatment with aqueous acetic acid, preferably 80% acetic acid at elevated temperature, around 80° C. $R_1'$ may also be phthalimido, which may be converted to amino by treatment with methyl hydrazine or hydrazine in an inert solvent, such as dichloromethane, at ambient temperature.

$R_2'$—$R_2$ a) $R_2$ may be protected amino, such as formylamino, which may be converted to $R_2$ is amino by hydrolysis.

$R_3'$—$R_3$ a) $R_3$ hydroxymethyl may be converted to $R_3$ acyloxymethyl by conventional acylation procedures.

b) $R_3'$ may be protected hydroxymethyl, which may be converted to $R_3$ hydroxymethyl by conventional deprotection methods.

Suitable examples of protecting groups and their removal, are as described in EP-A-242482. Particularly suitable protecting groups include the benzyl group, removed by catalytic hydrogenation using palladium/charcoal, 80% acetic acid; the acetate group removed by acid hydrolysis, 2M HCl in ethanol; or the t-butyldimethylsilyl group removable by 80% acetic acid at elevated temperature, around 90° C.

$R_4'—R_4$ a) When $R_5$ and $R_6$ in $R_4$ are other than hydrogen, they may be converted to $R_5$ and $R_6$ are hydrogen, using a deesterifying reagent, such as trimethylsilyl bromide in an aprotic solvent such as dichloromethane or dimethylformamide at ambient temperature, as described by C. E. McKenna et. al. J.C.S. Chem. Comm., 1979, 739.

Selective conversion of one $R_5$ and $R_6$ to hydrogen, may be achieved by treatment with hydroxide ion, as described by Rabinowitz JACS 1960, 82, 4564.

b) $R_4'$ may be hydrogen, which may be converted to $R_4$, by treatment with $QR_4$ wherein Q is a leaving group and $R_4$ is as defined. Q is preferably a tosyloxy group. Conditions for this reaction are i) preliminary formation of an alkoxide using a base, such as sodium hydride, in an aprotic solvent for example dimethylformamide ii) reaction with $QR_4$ at around ambient temperature. The reaction is as described A. Holy et. al. Collect. Czech. Chem. Comm. 1982, 47, 3447.

In this case, $R_5$ and $R_6$ are preferably other than hydrogen.

c) $R_4'$ may be hydrogen, which may be converted, when $R_3$ is hydroxymethyl, to $R_4$ is $CH_2PO(OH)(OR_5)$, by treatment with $ClCH_2PCl_2$ followed by treatment with a base, followed by $OR_5—$, according to the method described by A. Holy et. al. Czech. Chem. Comm. 1985, 50, 1507; ibid 1987, 52. 2775.

It will be appreciated that the above conversions may take place in any desired or necesssary order, having regard to the final desired compound of formula (I).

Intermediates of formula (II) may be prepared from a corresponding compound of formula (VI):

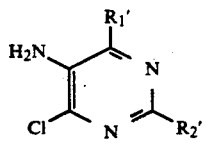

(VI)

and via intermediates of formula (V) wherein Z is OH, as hereinbefore defined, according to the methods described in EP-A-242482 i.e. by converting the compound of formula (V) wherein Z is OH to the phthalimidooxy derivative followed by reaction with methylhydrazine, as described in Descriptions 1 and 4 hereinafter.

The compound of formula (VI) wherein $R_1$ is chloro and $R_2$ is amino, is a known compound as described by Temple et. al. J. Org. Chem., 40 (21), 3141, 1975.

The compound of formula (VI) wherein $R_1$ is chloro and $R_2$ is hydrogen is a commercially available compound.

Intermediates of formula (III) may be prepared according to the methods described in EP-A-242482.

Compounds of the formula (IV) are prepared from compounds of formula (VI) wherein the 5-amino group is formulated by reaction with $R_9ONH_2$ wherein $R_9$ is a protecting group, to give a compound of formula (VII):

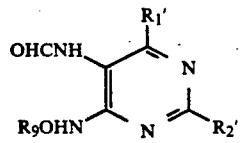

(VII)

which may be cyclised with diethoxymethyl acetate, to give a compound of formula (IV) wherein the OH group is protected. Suitable values for $R_9$ include benzyl, removable by hydrogenation, and the tetrahydropyran-2-yl group removable by treatment with 80% acetic acid, at ambient temperature.

Intermediates of the formula (V) wherein Z is hydroxy are known compounds or are prepared by analogous methods to those used for structurally similar known compounds.

It will be appreciated that, when $R_3$ is hydroxymethyl or acyloxymethyl in the resulting compound of formula (I), synthesis of the intermediate of formula (V) wherein Z is hydroxy may involve selective deprotection of an intermediate wherein Z is protected hydroxy and $R_3$ is protected hydroxymethyl, for example, as described in Description 4(b) hereinafter.

Intermediates of formulae (II), (III) and (V) but wherein Z is replaced by an aminooxy group, and wherein $R_4'$ is $R_4$ as defined in formula (I), are believed to be novel and form an aspect of the invention.

Intermediates of the formula (IV) wherein $R_1'$ is chloro and $R_2'$ is hydrogen are also believed to be novel and form an aspect of the invention.

Pharmaceutically acceptable salts may be prepared in conventional manner, for example, in the case of acid addition salts, by reaction with the appropriate organic or inorganic acid.

It will be appreciated that the invention provides a process for the preparation of a compound of formula (I) wherein $R_3$ is hydroxymethyl which process comprises the deprotection of a compound of formula (I) wherein an OH group in $R_3$ is in protected form. Preferred methods for deprotection, as hereinbefore described include removal of the benzyl, acetate or tbutyldimethylsilyl group.

The invention also provides a process for the preparation of a compound of formula (I) wherein $R_5$ and $R_6$ are both hydrogen, which process comprises the deesterification of a corresponding compound of formula (I) wherein $R_5$ and $R_6$ are the same alkyl or optionally substituted phenyl group.

The compounds of the invention are of potential use in the treatment of infections caused by viruses, especially herpesviruses such as herpes simplex type 1, herpes simplex type 2, varicella-zoster virus, Epstein-Barr virus and cytomegalovirus; and lentiviruses such as visna virus and human immunodeficiency virus (HIV 1 and 2)

The compounds may also be inhibitors of tumorogenic viruses and/or of potential use in the treatment of neoplastic diseases, i.e. cancer.

Compounds of the invention may be formulated for use in a pharmaceutical composition. Accordingly, in a further aspect of the invention, there is provided a pharmaceutical composition which comprises a compound of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia.

The composition for application to the eyes may be a conventional eye-drop composition well known in the art, or an ointment composition.

Preferably, the composition of this invention is in unit dosage form or in some other form that may be administered in a single dose. A suitable dosage unit might contain from 50 mg to 1 g of active ingredient, for example 100 to 500 mg.

Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day.

No unacceptable toxicological effects are indicated at the above described dosage levels.

The invention also provides a method of treating viral infections in a human or non-human animal, which comprises administering to the animal an effective, non-toxic amount of a compound of formula (I) or a pharmaceutically acceptable salt thereof.

The invention also provides a compound of formula (I) or a pharmaceutically acceptable salt thereof for use as an active therapeutic substance, in particular for the treatment of viral infections.

The compounds of the invention are also believed to exhibit a synergistic antiviral effect in conjunction with interferons; and combination products comprising these two components for sequential or concomitant administration, by the same or different routes, are therefore within the ambit of the present invention. The following examples illustrate the invention; the following descriptions illustrate the preparation of intermediates.

Description 1

Intermediates (V) for Examples 1 to 4

(a) Diethyl 2-hydroxyethoxymethylphosphonate

To a solution of diethyl 2-acetoxyethoxymethylphosphonate* (16 g, 63 mmol) in absolute ethanol (150 ml), was added 0.5M sodium ethoxide (12.19 ml). After standing at ambient temperature overnight, 1R-120H resin was added until pH 6.5 was reached. The solution was filtered immediately, the resin washed with ethanol and the combined filtrates evaporated under reduced pressure. The residue was chromatographed on silica gel (eluted with chloroform: methanol, 98:2) to yield the title compound as a colourless oil (9.3g, 70%). IR: $v_{max}$ (film) 3420, 3000, 1450, 1395, 1240, 1170, 1130, 1030, 970 cm$^{-1}$. $^1$H NMR: $\delta_H$ (CDCl$_3$) 1.35 (6H,t,J=7Hz, (OCH$_2$CH$_3$)$_2$), 3.75 (4H,br.s, OC$\underline{H}_2$C-H$_2$O), 3.90 (2H,d,$\overline{J}$=8Hz, O—C$\underline{H}_2$P), 4.20 ($\overline{4H}$,m,(O—CH$_2$CH$_3$)$_2$), 5.20 (1H,br.s, D$_2\overline{O}$ exchangeable, OH). Found: C,38.64; H,8.27%. C$_7$H$_{17}$PO$_5$.0.3-H$_2$O requires: C,38.63; H,8.01%.

(b) Diethyl 2-(N-phthalimidooxy)ethoxymethylphosphonate

Diethyl azodicarboxylate (8.12 g, 46.7 mmol) was added to a solution of diethyl 2-hydroxyethoxymethylphosphonate (9.0 g, 42.4 mmol), N-hydroxyphthalimide (6.92 g, 42.4 mmol) and triphenylphosphine (21.33 g, 46.7 mmol) in dry tetrahydrofuran (150 ml) at ambient temperature, under a nitrogen atmosphere. After 3 days, the mixture was evaporated to dryness, the residue dissolved in diethyl ether and the solution kept at 4° C. for 7 days. The cooled mixture was filtered and the filtrate evaporated to dryness. The residue was chromatographed on silica gel (eluted with hexane: ethyl acetate, 50:50 *Can.J.Chem.60, 547(1982); Chem. Abs. 55. 15507c 1961 to remove triphenylphosphine oxide, then changed to ethyl acetate) to give the title compound as a light orange coloured oil (10.6 g, 70%). IR: $v_{max}$ (film) 3510, 3000, 2950, 2920, 1795, 1745, 1735, 1430, 1380, 1250, 1190, 1165, 1130, 1030, 980, 880, 710 cm$^{-1}$. $^1$H NMR: $\delta_H$ (CDCl$_3$) 1.32 (6H,t,J=7Hz, (—OCH$_2$CH$_3$)$_2$), 3.93 (2H,d, J=8Hz, O—C$\underline{H}_2$P), 3.98 (2H,m,C$\underline{H}_2\overline{C}$H$_2$OCH$_2$P), 4.16 (4H,m, (OC$\underline{H}_2$CH$_3$)$_2$), 4.39 (2H,m,$\overline{N}$—OCH$_2$CH$_2$), 7.74–786 (4H,m,phthalyl H). Found: C,50.65; H,5.94; N,3.76%. C$_{15}$H$_{20}$NO$_7$P requires: C,50.42; H,5.64; N,3.92%. Found: m/z 358.1042(MH+). C15H$_{21}$NO$_7$P requires: m/z 358.1056.

c) Diethyl 2-(aminooxy)ethoxymethylphosphonate

To a solution of diethyl 2-(N-phthalimidooxy)ethoxymethylphosphonate (10.25 g, 29 mmol) in dry dichloromethane (55 ml) was added methylhydrazine (1.83ml, 34.4 mmol). After stirring at ambient temperature for 2 hours, the reaction mixture was filtered and evaporated to dryness. The residue was chromatographed on silica gel (eluted with dichloromethane: methanol 98:2) to give the title compound as an oil (6 g, 92%). IR: $v_{max}$ (film) 3480, 3320, 2995, 2920, 1600, 1445, 1390, 1370, 1240, 1170, 970 cm$^{-1}$. $^1$H NMR: $\delta_H$ (CDCl$_3$) 1.35 (6H,t,J=7Hz, (OCH$_2$CH$_3$)2), 3.8–3.95 (4H,m, O—CH$_2$CH$_2$O), 3.84 (2$\overline{H}$,d,J=8Hz, OCH$_2$P), 4.21 (4H,dq,$\overline{J}$=7Hz, 7Hz, (OCH$_2$CH$_3$)2), 4.8 (2$\overline{H}$,br.s, D$_2$O exchangeable, NH$_2$). Foun$\overline{d}$: C,36.58; H,7.98; N,6.22%. C$_7$H$_{18}$NO$_5$P requires: C,37.00; H,7.98; N,6.17%. Found: m/z 228.0987(MH+). C$_7$H$_{19}$NO$_5$P requires: m/z 228.1002.

Description 2

Intermediates for Examples 1 and 2 a) 4-Chloro-6-2-(diethoxyphosphorylmethoxy)ethoxyamino]-5-formamidopyrimidine

A mixture of 4,6-dichloro-5-formamidopyrimidine (1.9 g, 10 mmol), diethyl 2-(aminooxy)ethoxymethylphosphonate (2.27 g, 10 mmol) and triethylamine (2 ml, 15 mmol) in dry dioxan (50 ml) was heated at 100° C. for 4 hours. After cooling to ambient temperature, the reaction mixture was filtered and the filtrate concentrated under reduced pressure. The residual oil was chromatographed on silica gel (eluted initially with dichloromethane: methanol, 98:2, changed to dichloromethane; methanol, 95:5) to give the title compound as an oil (2.7 g, 70%). IR: $\nu_{max}$ (film) 3200, 2995, 1690, 1640, 1600, 1570, 1240, 1165, 1030 cm$^{-1}$. $^1$H NMR: $\delta_H$ [(CD$_3$)$_2$SO+D$_2$O] 1.33 (6H,t,J=7Hz, (OC$\underline{H}_2$CH$_3$)$_2$), 3.76 (2H,m, —C$\underline{H}_2$OC$\underline{H}_2$OP, 3.86 (2H,d,J=8Hz, OC$\underline{H}_2$P), 4.0–4.1 (6H,m, N—OC$\underline{H}_2$+(OC$\underline{H}_2$CH$_3$)$_2$), 8.15 (1H,s,H-2) Found: C,37.10; H,5.52; N,14.27%; m/z 382.0807(M+). C$_{12}$H$_{20}$N$_4$O$_6$PCl requires: C,37.66; H,5.27; N,14.64%; m/z 382.0809 (M+).

b) 6-Chloro-9-[2-(diethoxyphosphorylmethoxy)ethoxy]purine

A solution of 4-chloro-6-[2-(diethoxyphosphorylmethoxy)ethoxyamino]-5-formamidopyrimidine (2.4 g, 6.3 mmol) in diethoxymethyl acetate (10 ml) was heated at 120° C. for 45 minutes. After cooling to ambient temperature, the solvent was removed under reduced pressure. The residue was dissolved in methanol (15 ml) and 0.880 ammonia (1 ml). After 15 minutes, the reaction mixture was evaporated to dryness and the residue chromatographed on silica gel (eluted with dichloromethane: methanol, 98:2) to give the title compound as an oil (2.15 g, 94%). IR: $\nu_{max}$ (film) 3100, 3070, 2995, 1600, 1570, 1440, 1395, 1335, 1250, 1220, 1170, 1030, 930, 640 cm$^{-1}$. $^1$H NMR: $\delta_H$ [(CD$_3$)$_2$SO] 1.23 (6H,t,J=7Hz, (OCH$_2$C$\underline{H}_3$)$_2$), 3.88 (2H, d, J=8Hz, OC$\underline{H}_2$P), 3.89 (2H,m, C$\underline{H}_2$OCH$_2$P), 4.0–4.1 (4H,m, (OC$\underline{H}_2$CH$_3$)$_2$), 4.61 (2H,m,N—OC$\underline{H}_2$), 8.82 (1H,s,H-8), 8.97 (1H,s,H-2). Found: C,38.38; H,5.10; N,15.14%. C$_{12}$H$_{18}$N$_4$O$_5$PCl. 0.5H$_2$O requires: C,38.56; H,5.12; N,14.99%. Found: m/z 364.0703. C$_{12}$H$_{18}$N$_4$O$_5$PCl requires: m/z 364.0701.

Description 3

Intermediates for Examples 3, 4 (Method B) and 5 a) 4-Chloro-6-2-(diethoxyphosphorylmethoxy)ethoxyamino]-2,5-diformamidopyrimidine A mixture of 4,6-dichloro-2,5-diformamidopyrimidine (2.35 g, 10 mmol), diethyl 2-(aminooxy)ethoxymethylphosphonate (2.27 g, 10 mmol), and diisopropylethylamine (3.48 ml, 20 mmol) in diglyme (40 ml) was heated at 100° C. for 3 hours. After cooling to ambient temperature, the solvent was evaporated under reduced pressure and the residue obtained chromatographed on silica gel (eluted with dichloromethane methanol 97:3) to give the title compound as a yellow foam (2.8 g, 65%). $^1$H NMR: $\delta_H$ [(CD$_3$)$_2$SO] 1.26 (6H, t, J=7Hz, (OCH$_2$C$\underline{H}_3$)$_2$), 3.76 (2H, m C$\underline{H}_2$OCH$_2$P), 3.88 (2H, d, J=8Hz, OC$\underline{H}_2$P), 3.95–4.10 (6H, m, N—OC$\underline{H}_2$+(O—CH$_2$C$\underline{H}_3$)$_2$), 8.14 (1H, s, NHCHO), 9.16+9.41 (combined 1H, D$_2$O exchangeable N$\underline{H}$C$\underline{H}$O), 9.24 (1H, br.s, N$\underline{H}$CHO), 10.85 (2H, br.s, D$_2$O exchangeable, NHOC$\underline{H}_2$+N$\underline{H}$CHO).

b) 6-Chloro-9-[2-(diethoxyphosphorylmethoxy)ethoxy]-2-formamidopurine

A solution of 4-chloro-6-[2-(diethoxyphosphorylmethoxy) ethoxyamino]-2,5-diformamidopyrimidine (2.8 g, 6.6 mmol) in diethoxymethyl acetate (20 ml) was heated at 120° C. for 2 hours. After cooling to ambient temperature, excess solvent was removed under reduced pressure, the residue dissolved in methanol (20 ml) and 0.880 ammonia (6.5 ml) and the solution stirred at ambient temperature for 1 hour. The solvent was evaporated to leave an oil which was chromatographed on silica gel (eluted with dichloromethane: methanol, 98.2) to give the title compound as a pale yellow oil (2.4 g, 90%). IR: $\nu_{max}$ (film) 3480, 3120, 2995, 1710, 1610, 1580, 1510, 1440, 1390, 1330, 1240, 1050, 1030, 970, 920, 780 cm$^{-1}$; $^1$H NMR $\delta_H$ [(CD$_3$)$_2$SO] 1.23 (6H, t, J=7 Hz, (OCH$_2$C$\underline{H}_3$)$_2$), 3.87 (2H, d, J=8 Hz, OC$\underline{H}_2$P), 3.87 (2H, m, N-OCH$_2$C$\underline{H}_2$), 4.03 (4H, m, (OC$\underline{H}_2$CH$_3$)$_2$), 4.56 (2H, m, N-OC$\underline{H}_2$C$\underline{H}_2$), 8.75 (1H, s, H-8), 9.38 (1H, br.s, CHO), 11.30 (1H, br.s, D$_2$O exchangeable NHCHO). Found: C, 38.19; H, 4.79; N, 16.74%. C13H$_{19}$N$_5$O$_6$PCl requires: C, 38.29; H, 4.70; N, 17.17%. Found: m/z 408.0827 (MH+). C13H$_{20}$N$_5$O$_6$PCl requires: m/z 408.0840 (MH+).

Description 4

Intermediates (V) for Examples 6 (Method B), 7, 8, 9 (Method A) and 10 a) Diethyl [2-benzyloxy-1-(benzyloxymethyl)ethoxy]methylphoshonate

Dry HCl gas was bubbled through an ice-cooled solution of 1,3-dibenzyloxypropan-2-ol (25 g, 0.092 mol) and paraformaldehyde (2.75 g, 0.092 mol) in dry dichloromethane (100 ml) for 1 hour. The resulting solution was dried (MgSO$_4$) and evaporated to dryness to leave an oil. Triethyl phosphite (15.7 ml, 0.092 mol) was added and the resulting mixture stirred and heated at 140° C. for 16 hours. The liquid obtained was dissolved in ethyl acetate and washed with sodium bicarbonate solution. The organic phase was washed with brine, dried (MgSO$_4$) and evaporated to give a mobile oil, which was chromatographed in silica (hexane/ethyl acetate 50:50 as eluant) to give the title compound as a colourless, mobile oil (19.7 g, 51). IR: $\nu_{max}$ (film) 3055, 3020, 2900, 2860, 1490, 1470, 1450, 1390, 1305, 1255, 1095, 1050, 1030, 970, 820, 770, 735, 700 cm$^{-1}$. $^1$H NMR: $\delta_H$(CDCl$_3$) 1.3 (6H, t, J=7 Hz, P-(OCH$_2$C$\underline{H}_3$)$_2$), 3.6 (4H, d, 2×C$\underline{H}_2$OCH$_2$Ph),3.8–4.05 (1H, m, C$\underline{H}$), 4.05 (2H, d, J=9 Hz, OC$\underline{H}_2$P), 4.0–4.3 (4H, m, P-(OC$\underline{H}_2$CH$_3$)$_2$), 4.55 (4H, s, 2×OC$\underline{H}_2$Ph), 7.38 (10H, s, 2×P$\underline{h}$). C$_{22}$H$_{31}$PO$_6$ requires: C, 62.54; H, 7.42. Found: C, 62.75, H, 7.61. m/z: C$_{22}$H$_{31}$PO$_6$ requires 422.1858; observed (M+) 422.1864.

b) Diethyl [2-hydroxy-1-(hydroxymethyl)ethoxy]methylphosphonate and Diethyl [2-benzyloxy-1-(hydroxymethyl)ethoxy]methylphosphonate To a solution of diethyl [2-benzyloxy-1-(benzyloxymethyl)ethoxy]methylphosphoate (15.5 g, 36.7 mmol) in ethanol (200 ml), containing a trace of methanolic HCl (1 ml), was added 10% Pd-C (1.5 g). The mixture was treated with hydrogen at atmospheric temperature and pressure for a total of 6 days. Filtration and evaporation of the solvent gave an oil which was chromatographed on silica (eluant dichloromethane/methanol 95:5, then 92:8) after which were obtained the monobenzyl ether (3.65 g, 30%) and the diol (2.73 g, 30%).

Data for diol. IR: $\nu_{max}$ (film) 3400, 2980, 2940, 2920, 1650, 1480, 1445, 1390, 1370, 1295, 1230, 1165, 1120, 1020, 980, 880, 820, 780 cm$^{-1}$. $^1$H NMR: $\delta_H$[(CD$_3$)$_2$SO] 1.23 (6H, t, J=7 Hz, (OCH$_2$C$\underline{H}_3$)$_2$), 3.25–3.6 (5H, m, C$\underline{H}_2$C$\underline{H}$C$\underline{H}_2$), 3.94 (2H, d, J=8.2 Hz, OC$\underline{H}_2$P), 4.0–4.2 (4$\underline{H}$, m, (OC$\underline{H}_2$CH$_3$)$_2$), 4.56 (2H, br.s, D$_2$O exchangeable, 2×OH). m/z: C$_8$H$_{20}$O$_6$P requires: 243.0998; observed 243.0986 (M+H+). Data for monobenzyl ether.

IR: $\nu_{max}$ (film) 3395, 2980, 2900, 2860, 1475, 1450, 1390, 1365, 1240, 1160, 1090, 1050, 1020, 970, 810, 775, 730, 695 cm$^{-1}$. $^1$H NMR: $\delta_H$ [(CD$_3$)$_2$SO] 1.21, 1.20 (6H, 2×t, J=7 Hz, 7 Hz, (O-CH$_2$CH$_3$)$_2$) 3.5–3.7 (5H, m, CH$_2$CHCH$_2$-), 3.95 (2H, d, d, J=8.8 Hz, OCH$_2$P), 4.0 (4H, m, (OCH$_2$CH$_3$)$_2$), 4.49 (2H, s, OCH$_2$Ph), 4.68 (1H, t, D$_2$O exchangeable OH), 7.2–7.5 (5H, m, Ph). C$_{15}$H$_{25}$O$_6$P. 0.4 H$_2$O requires: C, 53.06; H, 7.67. Found: C, 53.11; H, 7.94. m/z: C$_{15}$H$_{26}$O$_6$P requires 333.1467, observed: 333.1472 (M+H$^+$).

c) Diethyl 2-benzyloxy-1-(N-phthalimidooxymethyl-)ethoxy]methylphosphonate

Diethyl azodicarboxylate (1.82 ml, 11.6 mmol) was added to a solution of diethyl [2-benzyloxy-1-(hydroxymethyl) ethoxy]methylphosphonate (3.5 g, 10.5 mmol), N-hydroxyphthalimide (1.72 g, 10.5 mmol) and triphenylphosphine (3.04 g, 11.6 mmol) in dry THF (60 ml). The reaction mixture was left at ambient temperature for 5 days, then evaporated to dryness. The residue obtained was dissolved in diethyl ether and left at 5° C. for 16 hours. The precipitated crystals of triphenylphosphine oxide were filtered off and the ether filtrate evaporated to dryness to leave an oil. After chromatography on silica gel (eluant hexane/ethyl acetate 50:50, then 30:70, then 20:80) the title compound was obtained as a colourless oil (4.1 g, 80%). IR: $\nu_{max}$ (film) 3060, 3020, 2980, 2930, 2920, 1790, 1740, 1465, 1450, 1370, 1250, 1190, 1160, 1130, 1100, 1080, 1050, 1030, 970, 870, 820, 780, 740, 700 cm$^{-1}$. $^1$H NMR: $\delta_H$ (CDCl$_3$) 1.30 (6H, t, J=7 Hz, (OCH$_2$CH$_3$)$_2$), 3.7 (2H, d, J=5H$_z$, CHCH$_2$OCH$_2$Ph), 4.0–4.25 (7H, m, (OCH$_2$CH$_3$)$_2$, OCH$_2$Ph, CH$_2$CHCH$_2$), 4.36 (2H, m, CH$_2$ON), 4.56 (2H, s, OCH$_2$Ph), 7.30–7.35 (5H, br.s, Ph), 7.74–7.9 (4H, m, phthalimide aromatic H). m/z: C$_{23}$H$_{28}$NO$_8$P requires 477.1553; observed: 477.1548 (M+).

d) Diethyl (1-aminooxymethyl-2-bezyloxyethoxy)-methylphosphonate

To a solution of diethyl [2-benzyloxy-1-(N-phthalimidooxymethyl)ethoxy]methylphosphonate, (4 g, 8.4 mmol) in dry dichloromethane (40 ml), was added methylhydrazine (0.54 ml, 10.1 mmol) at ambient temperature and the mixture stirred for 2 hours. The solution was filtered and the filtrate evaporated to dryness. The residue was dissolved in ether and left at 5° C. overnight. The deposited solid was filtered off, the filtrate evaporated and the residue chromatographed on silica (eluant dichoromethane/methanol 98:2) to give the title compound as a colourless oil (2.7 g, 92%). $^1$H NMR: $\delta_H$(CDCl$_3$) 1.32, 1.33 (6H, 2xt, P-(OCH$_2$CH$_3$)$_2$), 3.5–3.65 (2H, m, CHONH$_2$), 3.78 (2H, d, CH$_2$OCH$_2$Ph), 3.95–4.1 (3H, m, OCH$_2$P+CH$_2$CHCH$_2$), 4.1–4.3 (4H, m, P-(OCH$_2$CH$_3$)$_2$), 4.53 (2H, s, OCH$_2$Ph), 5.0–6.0 (2H, br.s, D$_2$O exchangeable, NH$_2$), 7.27–7.35 (5H, m, aromatic H). m/z: C$_{15}$H$_{26}$NO$_6$P requires 347.1498; observed 347.1516 (M+).

DESCRIPTION 5

Intermediates for Examples 6 (Method B), 7 and 8 a) 6-[3-Benzyloxy-2-(diethoxyphosphorylmethoxy)-propoxyamino-4-chloro-5-formidopyrimidine A mixture of 4,6-dichloro-5-formamidopyrimidine (390 mg, 2 mmol), diethyl (1-aminooxymethyl-2-benzyloxyethoxy)methylphosphonate (700 mg, 2 mmol) and triethylamine (0.41 ml, 3 mmol) in dry dioxan (5 ml) was heated at 100° C. for 2 hours. The reaction mixture was cooled, filtered and the filtrate evaporated to leave a yellow oil which was chromatographed on silica (dichloromethane/methanol 98:2 as eluant) to give the title compound as a yellow viscous oil (750 mg, 74%), $^1$H NMR: $\delta_H$ [(CD$_3$)$_2$SO+D$_2$O] 1.30 (6H, t, J=7 Hz, (OCH$_2$CH$_3$)$_2$), 3.55–3.8 (2H, m, CH$_2$OCH$_2$Ph), 3.9–4.2 (9H, m, (OCH$_2$CH$_3$)$_2$+OCH$_2$P+NHOCH$_2$CH), 4.6 (2H, s, OCH$_2$Ph), 7.42 (m, 5H, aromatic Ph), 8.24 (1H, s, H-2). Found: C, 47.66; H,5.69; N, 10.51%. C$_{26}$H$_{28}$N$_4$O$_7$PCl requires: C, 47.76; H, 5.61; N,11.14%, m/z: C$_{20}$H$_{28}$N$_4$O$_7$PCl requires: 502.1384; observed: 502.1340 (M+).

b) 9-[3-Benzyloxy-2-(diethoxyphosphorylmethoxy)-propoxy-6-chloropurine

A solution of 6-[3-benzyloxy-2-(diethoxyphosphorylmethoxy)propoxyamino]-4-chloro-5-formamidopyrimidine (750 mg, 1.49 mmol) in diethoxymethyl acetate (2 ml) was stirred and heated at 120° C. for 2 hours. After cooling to ambient temperature, the excess solvent was evaporated. The residue was dissolved in methanol (10 ml) and 0.880 ammonia (1 ml) and left at ambient temperature for 10 minutes. The solvent was removed under reduced pressure and the residue chromatographed on silica (dichloromethane/methanol, 98:2 as eluant) to give the title compound as a yellow oil (590 mg, 80%). IR: $\nu_{max}$ (film) 3060, 2990, 2905, 1590, 1565, 1435, 1330, 1250, 1220, 1165, 1100, 1050, 1030, 970, 930, 850 cm$^{-1}$. $^1$H NMR: $\delta_H$ [(CD$_3$)$_2$SO] 1.21 (6H, t, J=7 Hz, (OCH$_2$CH$_3$)$_2$), 3.6–3.75 (2H, m, CH$_2$OCH$_2$Ph) 3.8–4.1 (7H, m, (OCH$_2$CH$_3$)$_2$+OCH$_2$P+CH$_2$CHCH$_2$), 4.53 (2H, s, OCH$_2$Ph), 4.5–4.7 (2H, m, N-OCH$_2$), 7.32 (5H, br.s, Ph), 8.82 (1H, s), 9.02 (1H, s) Found: C, 49.71; H, 5.68; N, 10 94%. C$_{20}$H$_{26}$N$_4$O$_6$PCl requires: C, 49.54; H, 5.40; N, 11.56%. m/z: C$_{20}$H$_{26}$N$_4$O$_6$PCl$^*$ requires 484.1279; observed 484 1249 (M+).

c) 9-[3-Benzyloxy-2-(diethoxyphosphorylmethoxy)-propoxy]adenine

A solution of 9-[3-benzyloxy-2-(diethoxyphosphorylmethoxy)propoxy]-6-chloropurine (570 mg, 1.18 mmol) in ethanolic ammonia (10 ml) was heated in a sealed vessel at 110° C. for 2 hours. After cooling to ambient temperature, the solvent was evaporated and the residue obtained chromatographed on silica (dichloromethane/methanol 95:5 as eluant) to give the title compound (350 mg, 64%). IR: $\nu_{max}$ (film) 3320, 3200, 2980, 2900, 640, 1595, 1470, 1450, 1410, 1390, 1370, 1330, 1290, 1240, 1160, 1090, 1050, 1020, 970, 820, 790, 730, 700, cm$^{-1}$. $^1$H NMR: $\delta_H$ [(CD$_3$)$_2$SO] 1.22 (6H, t, J=7 Hz, OCH$_2$CH$_3$)$_2$), 3.6–3.75 (2H, m, CH$_2$OCH$_2$Ph), 3.95–4.2 (7H, m, (OCH$_2$CH$_3$)$_2$+CH$_2$CHCH$_2$+OCH$_2$P), 4.4–4.65 (2H, m, N-OCH$_2$), 4.52 (2H, s, OCH$_2$Ph), 7.25–7.4 (5H, m, aromatic), 7.39 (2H, br.s, D$_2$O exchangeable NH$_2$), 8.15(1H, s), 8.41 (1H, s). Found: C, 49.81; H, 5.75; N, 14.07%; C$_{20}$H$_{28}$N$_5$O$_6$P. H$_2$O requires: C, 49.68; H, 6.25; N, 14.48%, m/z: C$_{20}$H$_{28}$N$_5$O$_5$P requires 465.1777; observed: 467.1757.

DESCRIPTION 6

Intermediates for Examples 9 (Method A) and 10 a) 6-[3-Benzyloxy-2-(diethoxyphosphorylmethoxy)-propoxyamino]-4-chloro-2,5-diformamidopyrimidine A mixture of 4,6-dichloro-2-5-diformamidopyrimidine (650 mg, 2.74 mmol), diethyl (1-aminooxymethyl-2-benzyloxyethoxy)methylphosphonate (950 mg, 2.74 mmol) and diisopropylethylamine (0.95 ml, 5.5 mmol) in diglyme (12 ml) was heated at 100° C. for 2½ hours. The mixture was cooled and the solvent evaporated to leave an oily residue which was chromatographed on silica (dichloromethane/methanol 97:3 as eluant) to give the title compound as a yellow foam (800 mg, 54%). $^1$H NMR: $\delta_H$ [(CD$_3$)$_2$SO] 1.21 (6H, 2×t, P-(OCH$_2$CH$_3$)$_2$), 3.5–3.7 (2H, m, CH$_2$OCH$_2$Ph), 3.75–4.2 (9H, m, (OCH$_2$CH$_3$)$_2$+OCH$_2$CH+OCH$_2$P), 4.51 (2H, s, OCH$_2$Ph), 7.25–7.5 (5H, m, Ph), 8.15 (1H, s, CHO), 9.26 (1H, br.s, CHO), 9.44–10.88 (3H, 2×br.s, D$_2$O exchangeable NH+2×NHCHO). Found: C, 46.32; H, 5.61; N, 11.94% C$_{21}$H$_{29}$N$_5$O$_8$PCl requires: C, 46.20; H, 5.35; N, 12.83%. m/z: 545 (M+).

b) 9-[3-Benzyloxy-2-(diethoxyphosphorylmethoxy)-propoxy]-6-chloro-2-formamidopurine A solution of 6-[3-benzyloxy-2-(diethoxyphosphorylmethoxy)propoxyamino]-4-chloro-2,5-diformamidopyrimidine (760 mg, 1.4 mmol) in diethoxymethyl acetate (2 ml) was stirred and heated in an oil bath at 120° C. for 2 hours. After cooling to ambient temperature, the solvent was evaporated and the residue dissolved in methanol (10 ml) and 0.880 ammonia (1 ml). After 15 minutes at ambient temperature the solution was evaporated to dryness. The residue obtained was chromatographed on silica gel (dichloromethane/methanol, 98:2 as eluant) to give the title compound as a colourless oil (550 mg, 75%). IR: $\nu_{max}$ (film), 3400, 3220, 3110, 2980, 2900, 1710, 1610, 1580, 1510, 1475, 1440, 1385, 1330, 1240, 1160, 1140, 1095, 1050, 1020, 980, 920, 820, 780, 740, 700 cm$^{-1}$. $^1$H NMR: $\delta_H$ [(CD$_3$)$_2$SO] 1.20, 1.21 (6H, 2×t, P-(OCH$_2$CH$_3$)$_2$), 3.6–3.75 (2H, m, CHCH$_2$), 3.8–4.15 (7H, m, CH$_2$CHCH$_2$, OCH$_2$P, P-(OCH$_2$CH$_3$)$_2$), 4.52 (2H, s, OCH$_2$Ph), 4.45–4.65 (2H, m, N-OCH$_2$), 7.25–7.40 (5H, m, Ph), 8.81 (1H, s, H-8), 9.37 (1H, br.s, NHCHO), 11.31 (1H, br.s, D$_2$O exchangeable NHCHO). Found: C, 48.11; H, 5 37; N, 12.50%. C$_{21}$H$_{27}$N$_5$O$_7$PCl requires: C, 47.77; H, 5.16; N, 13.27%. m/z: C$_{21}$H$_{28}$N$_5$O$_7$PCl requires 528.1415; observed 528.1363 (M +H+).

c) 9-[3-Benzyloxy-2-(diethoxyphosphorylmethoxy)-propoxy]guanine

A solution of 9-[3-benzyloxy-2-(diethoxyphosphorylmethoxy)propoxy]-6-chloro-2-formamidopurine (520 mg, 1 mmol) in 80% aqueous formic acid (6 ml) was stirred and heated at 80° C. for 5 hours. After cooling and evaporation to dryness, the residue was dissolved in methanol (5 ml) and 0.880 ammonia (1 ml). After 15 minutes at ambient temperature, the solvent was evaporated and the residue obtained chromatographed on silica gel (dichloromethane/methanol 90:10 as eluant) to give the title compound as a white solid (330 mg, 70%), mp. 166°–169° (acetone). IR: $\nu_{max}$ (KBr) 3326, 3167, 2983, 2907, 2868, 2745, 1694, 1648, 1600, 1586, 1540, 1475, 1454, 1391, 1328, 1251, 1163, 1100, 1051, 1027, 970, 823, 787, 739, 693, 624, cm$^{-1}$. UV: $\lambda_{max}$ (EtOH) 255 nm (14,100), $^1$H NMR: $\delta_H$ [(CD$_3$)$_2$SO], 1.22 (6H, 2×t, J=7 Hz, P-(OCH$_2$CH$_3$)$_2$), 3.5–3.8 (2H, m, CH$_2$OCH$_2$Ph), 3.85–4.25 (7H, m, OCH$_2$P, P-(OCH$_2$CH$_3$)$_2$, CH$_2$CHCH$_2$), 4.3–4.5 (2H, m, N-OCH$_2$), 4.50 (2H, s, OCH$_2$Ph), 6.58 (2H, br.s, D$_2$O exchangeable NH$_2$), 7.25–7.5 (5H, m, Ph), 7.95 (1H, s, H-8), 10.69 (1H, br.s, D$_2$O exchangeable NH). Found: C, 49.35; H, 5.85; N, 14.60%. C$_{20}$H$_{28}$N$_5$O$_7$P. O.25H$_2$O requires: C, 49.43; H, 5.91; N, 14.41%. m/z: (FAB, matrix thioglycerol)$_{482}$ (M+H+).

DESCRIPTION 7

Intermediates (V) for Examples 6 (Methods A and C). 7, 8, 9 (Method B), 10 15 and 16 a) Diethyl 2-acetoxy-1-(hydroxymethyl)ethoxy]methylphosphonate

To a solution of diethyl [2-hydroxy-1-(hydroxymethyl)ethoxy] methylphosphonate (6.1 g, 25.2 mmol) in dry THF (75 ml) were added p-toluenesulphonic acid (250 mg) and trimethyl orthoacetate (4.45 ml, 35 mmol). The reaction mixture was stirred at ambient temperature for 16 hours after which water (1 ml) plus 2MHCl (5 drops) were added. After stirring for a further 30 minutes, the solution was evaporated to dryness and the residue chromatographed on silica gel (eluant dichloromethane: methanol 97:3) to give the title compound (5.1 g, 71%) as colourless mobile oil. IR: $\nu_{max}$ (film) 3400, 2980, 2920, 2910, 1740, 1440, 1390, 1370, 1245, 1160, 1120, 1050, 1030, 970, 820, 780 cm$^{-1}$. $^1$H NMR: $\delta_H$ (CDCl$_3$) 1.36 (6H, t, J=7 Hz, P(OCH$_2$CH$_3$)$_2$), 2.10 (3H,s, COCH$_3$), 3.65–4.50 (12H,m, P(OCH$_2$CH$_3$)$_2$, OCH$_2$P, OCH$_2$CHCH$_2$OH). Found: C,41.79; H,7.66%. C$_{10}$H$_{21}$O$_7$P requires: C,42.25; H,7.66%. m/z: (Isobutane C.I) 285 (MH+, 100%).

b) Diethyl [2-acetoxy-1-(N-phthalmidooxymethyl)ethoxy]methylphosphonate

Diethyl azodicarboxylate (1.89 ml, 12 mmol) was added to a solution of diethyl [2-acetoxy-1-(hydroxymethyl)ethoxy]methylphosphonate (3.1 g, 10.9 mmol), triphenylphosphine (3.15 g, 12 mmol) and N-hydroxyphthalimide (1.78 g, 10.7 mmol) in dry THF (60 ml). The reaction mixture was stirred at ambient temperature under an atmosphere of nitrogen for 16 hours, and then evaporated to dryness. The residue obtained was dissolved in diethyl ether and left at 4° C. for 16 hours. The crystals of triphenylphosphine oxide were removed by filtration and the filtrate evaporated to dryness. The residue was chromatographed on silica gel (eluant hexane:acetone 70:30) to give the title compound as a pale yellow oil (3.6 g, 76). IR: $\nu_{max}$ (film) 3500, 3460, 2980, 2900, 1780, 1735, 1465, 1440, 1370, 1240, 1185, 1160, 1030, 1020, 970, 875, 820, 780, 700 cm$^{-1}$. $^1$H NMR: $\delta_H$ (CDCl$_3$) 1.33 (6H,2×t, J=7 Hz, (OCH$_2$CH$_3$)$_2$), 2.09 (3H,s, COCH$_3$), 3.9–4.5 (11H,m, (OCH$_2$CH$_3$)$_2$, +OCH$_2$P,+OCH$_2$CHCH$_2$), 7.75–7.87 (4H,m, aromatic H). Found: C,50.14; H,5.69%; N, 3.15%. C$_{18}$H$_{24}$NO$_9$P requires: C,50.35; H,5.63; N, 3.26%. m/z: observed 430.1275; C$_{18}$H$_{25}$NO$_9$P (MH+) requires 430.1267.

c) Diethyl [2-acetoxy-1-(aminooxymethyl)ethoxyl]methylphosphonate

To a solution of diethyl [2-acetoxy-1-(N-phthalimidooxymethyl)ethoxy]methylphosphonate (1.0 g. 2.33 m mol), in dry dichloromethane (20 ml) was added methylhydrazine (0.125 ml, 2.35 mmol) and the solution stirred at ambient temperature for 10 minutes. The reaction mixture was filtered, and the filtrate evaporated to dryness. The residue obtained was chromatographed on silica gel (eluant dichloromethane methanol 98:2) to give the title compound as a colourless oil (0.59 g, 86%). IR: $\nu_{max}$ (film) 3460, 3320, 3240, 3170, 2995, 2910, 1740, 1595, 1445, 1390, 1370, 1240, 1165, 1115, 1050, 1025, 975, 820, 780 cm$^{-1}$. $^1$H NMR: $\delta_H$ [(CD$_3$)$_2$SO] 1.23 (6H,t, J=7 Hz, (OCH$_2$CH$_3$)$_2$), 2.02 (3H,s, COCH$_3$), 3.5–3.65 (2H,m, NOCH$_2$), 3.8–4.25 (9H,m, OCH$_2$P) (OCH$_2$CH$_3$)$_2$+CHCH$_2$), 6.13 (2H br. s, D$_2$O exchangeable NH$_2$). Found: C,39.52; H,7.20; N,4.46%; C$_{10}$H$_{22}$NO$_7$P requires: C,40.13; H,7.41; N, 4.68%. m/z: observed 299.1117; C$_{10}$H$_{22}$NO$_7$P (M+) requires 299.1134.

DESCRIPTION intermediates for Examples 6 (Method A), 7 and 8 a) 6-[[3-Acetoxy-2-(diethoxyphosphorylmethoxy)-propoxy]amino]-4-chloro-5-formamidopyrimidine A mixture of 4,6-dichloro-5-formamidopyrimidine (0.77 g, 4.0 mmol), diethyl [2-acetoxy-1-(aminooxymethyl)ethoxy]methylphosphonate (1.2 g, 4.0 mmol) and triethylamine (0.82 ml, 6 mmol) in dry dioxan (20 ml) was heated at 100° C. for 2 hours. The reaction mixture was cooled, filtered, and the filtrate evaporated to leave an oil which was chromatographed on silica gel (eluant dichloromethane:methanol 97:3) and gave the title compound as a yellow oil (1.08 g, 60%). $^1$H NMR: $\delta_H$ [(CD$_3$)$_2$SO] 1.23 (6H,t, J=7 Hz, (OCH$_2$C$\underline{H}_3$)$_2$), 2.03 (3H,s, COC$\underline{H}_3$), 3.85–4.35 (11H,m, (OC$\underline{H}_2$CH$_3$)$_2$+OC$\underline{H}_2$P+OC$\underline{H}_2$CHC$\underline{H}_2$O). m/z: observed 454.1020; C$_{15}$H$_{24}$N$_4$O$_8$PCl (M+) requires 454.0996.

b) 9-3-Acetoxy-2-(diethoxyphosphorylmethoxy)-propoxy]-6-chloropurine

A solution of 6-[[3-acetoxy-2-(diethoxyphosphorylmethoxy)propoxy]amino]-4-chloro-5-formamidopyrimidine (0.80 g, 1.76 mmol) in diethoxymethyl acetate (5 ml) was heated at 120° C. for 2 hours. After cooling to ambient temperature, the excess solvent was evaporated under reduced pressure. The residue obtained was dissolved in methanol (5 ml) and .880 ammonia (1 ml) and left at ambient temperature for 10 minutes. The solvent was removed under reduced pressure and the residue chromatographed on silica gel (eluant dichloromethane:methanol 98:2) to give the title compound as a yellow oil (0.68 g, 88). IR: $\nu_{max}$ (film) 3080, 3050, 2990, 2900, 1740, 1640, 1590, 1565, 1435, 1390, 1370, 1330, 1240, 1160, 1120, 1040, 1025, 970, 930, 850, 820, 780 cm$^{-1}$. $^1$M NMR: $\delta_H$ [(CD$_3$)$_2$SO] 1.23 (6H,t, J=7 Hz, (OCH$_2$C$\underline{H}_3$)$_2$). 2.04 (3H,s, COC$\underline{H}_3$), 3.95–4.15 (7H,m, (OC$\underline{H}_2$P+(OC$\underline{H}_2$CH$_3$)$_2$+C$\underline{H}$), 4.20 (1H,dd, J=5.22 Hz, J=12.1 Hz, C$\underline{H}_B$OAc), 4.36 (1H,dd, J=3.85 Hz, J=12.1 Hz, C$\underline{H}_A$OAc), 4.55 (1H,dd, J=6.05 Hz, J=11.55 Hz, N-OC$\underline{H}_B$), 4.70 (1H,dd,J=3.58 Hz, J=11.55 Hz, N-OC$\underline{H}_A$), 8.83 (1H,s), 9.04(1H,s). Found: C,41.38; H,5.13; N,12.39%; C$_{15}$H$_{22}$N$_4$O$_7$PCl requires: C,41.24; H,5.08; N,12.83%. m/z: (FAB, thioglycerol matrix) 437 (MH+).

DESCRIPTION 9

Intermediates for Example 16 a) 6-[[3-Acetoxy-2-(diethoxyphosphorylmethoxy)-propoxy]amino]-4-chloro-2,5-diformamidopyrimidine A mixture of 4,6-dichloro-2,5-diformamidopyrimidine (0.475 mg, 2 mmol), diethyl [2-acetoxy-1-(aminooxymethyl)ethoxy)methylphosphonate (0.60 mg, 2 mmol) and triethylamine (0.54 ml, 4 mmol) in dry dioxan (20 ml) was heated at 120° C. for 5 hours. The reaction mixture was cooled to ambient temperature, filtered, and the filtrate evaporated to leave a yellow oil. The oil was chromatographed on silica gel (eluant dichloromethane:methanol 97:3) to give the title compound as a pale yellow solid (0.81 g, 80%). $^1$H NMR: $\delta_H$ [(CD$_3$)$_2$SO] 1.23 (2×3H, 2×t, J=7 Hz, (OCH$_2$C$\underline{H}_3$)$_2$), 2.03 (3H,s, COC$\underline{H}_3$), 3.80–4.35 (11H,m, C$\underline{H}_2$CHC$\underline{H}_2$+(OC$\underline{H}_2$CH$_3$)$_2$+OC$\underline{H}_2$P), 8.16 (1H,br.s, sharpens to s. on D$_2$O, C$\underline{H}$O), 9.26 (1H,d,J=9.9 Hz. collapses to s. on D$_2$O. C$\underline{H}$O), 9.45 (1H,br.s, D$_2$O exchangeable, N$\underline{H}$), 10.8–10.95 (2H,m, D$_2$O exchangeable 2×N$\underline{H}$). Found: C,37.36; H,5.37; N,13.43%; C$_{16}$H$_{25}$N$_5$O$_9$PCl.H$_2$O requires: C,37.18; H,5.27; N,13.55%. m/z: observed 497.1082; C$_{16}$H$_{25}$N$_5$O$_9$PCl(M+) requires 497.1078.

b) 9-[3-Acetoxy-2-(diethoxyohosphorylmethoxy)-propoxy]-6-chloro-2-formamidopurine A solution of 6-[[3-acetoxy-2-(diethoxyphosphorylmethoxy)propoxy]amino]-4-chloro-2,5-formamidopyrimidine (0.30 g, 0.66 mmol) in diethoxymethyl acetate (5 ml) was heated at 120° C. for 3 hours. After cooling to ambient temperature, excess solvent was removed under reduced pressure. The residue obtained was dissolved in methanol (2 ml) and 0.880 ammonia (0.5 ml) and left at ambient temperature for 15 minutes. The solvent was removed under reduced pressure and the residue obtained chromatographed on silica gel (eluant dichloromethane:methanol 97:3) to give the title compound as a colourless gum (0.20 g, 63%). $^1$H NMR: $\delta_H$ [(CD$_3$)$_2$SO] 1.22 (2×3H, 2×t,J=7 Hz, (OCH$_2$C$\underline{H}_3$)$_2$), 2.04 (3H,s, COC$\underline{H}_3$), 3.75–4.20 (7H,m, (OC$\underline{H}_2$C$\underline{H}_3$)-2+OC$\underline{H}_2$P, C$\underline{H}$), 4.21 (1H,dd, J=5.22 Hz, J=12.10 Hz, CH$_B$OAc), 4.38 (1H,dd, J=3.85 Hz, J=12.10 Hz, CHOAc), 4.50 (1H,dd, J=6.05 Hz, J=11.55 Hz, NOC$\underline{H}_B$), 4.63 (1H,dd, J=3.57 Hz, J=11.55 Hz,NO-C$\underline{H}_A$), 8.82 (1H,s, H-8), 9.38 (1H,d, J=9.6 Hz, collapses to s. on D$_2$O, C$\underline{H}$O), 11.32 (1H,d,J=9.6 Hz, D$_2$O exchangeable N$\underline{H}$).

DESCRIPTION 10

Intermediates for Examples 6 (Method A), 7 and 8 a) 9-Benzyloxy-6-chloropurine

A mixture of 4,6-dichloro-5-formamidopyrimidine (58.6 g; 0.31 mmol), benzyloxyamine (37.5 g; 0.31 mmol), triethylamine (110 ml) and dioxan (400 ml) was stirred at 100° C. for 4 hours. The reaction was cooled, filtered and evaporated under reduced pressure. The residue was partitioned between ethyl acetate (750 ml), saturated aqueous potassium bicarbonate (400 ml) and brine (200 ml). The organic phase was separated and the aqueous phase washed with ethyl acetate (300 ml). The combined organic phases were washed with water (200 ml), brine (200 ml), dried (MgSO$_4$), and evaporated under reduced pressure.

The residue was dissolved in anhydrous N,N-dimethylformamide (100 ml), triethyl orthoformate (200 ml), and 12N hydrochloric acid (5 ml). After 4 hours at 25° C. the solvent was removed under reduced pressure. The residue was partitioned between chloroform (750 ml) and saturated aqueous potassium bicarbonate (500 ml). The resulting suspension was filtered and the phases separated. The organic phase was washed with saturated potassium bicarbonate (200 ml), water (200 ml), dried (MgSO$_4$) and evaporated under reduced pressure. The residue was purified by column chromatography on silica gel eluting with chloroform-methanol (100:1), affording the title compound (38.4 g, 48%). IR: $\nu_{max}$ (KBr) 3350, 1587, 1565, 1438 cm$^{-1}$; $^1$H NMR: $\delta_H$ (CDCl$_3$) 5.40(2H, s, C$\underline{H}_2$Ar), 7.35(5H, s, Ar), 7.75(1H, s, H-8), 9.85(1H, s, H-2). Found: C, 55.11; H, 3.73; N, 21.27%. C$_{12}$H$_9$N$_4$OCl requires: C, 55.28; H, 3.49, N, 21.50%.

b) 9-Benzyloxyadenine

A solution of 9-benzyloxy-6-chloropurine (38.4 g; 0.147 mmol) in ethanol (300 ml) saturated with ammonia was heated at 100° C. in an autoclave for 16 hours. After cooling the suspension was evaporated to dryness and the residue partitioned between chloroform (750 ml) and water (500 ml). The separated aqueous phase was washed with chloroform (200 ml). The combined organic phases were washed with water, dried (MgSO$_4$) and evaporated, affording an orange solid homogeneous on t.l.c. (31.1 g, 87%). IR: $\nu_{max}$ (KBr) 3372, 3300, 3187, 3038, 1660, 1637, 1600, 1581 cm$^{-1}$; $^1$H NMR: $\delta_H$ [(CD$_3$)$_2$SO] 5.3(2H, s, CH$_2$Ar), 6.8(2H, br.s, D$_2$O exchangeable, NH$_2$), 7.3(6H, s, H-8, Ar), 7.7(1H, s, H-2). Found: C, 59.39; H, 4.60; N, 29.07%; m/e 241 0949. C$_{12}$H$_{11}$N$_5$O requires: C, 59.73; H, 4.60; N, 29.03%; m/z 241.0964.

c) 9-Benzyloxy-6-phthalimidopurine

Phthaloyl dichloride (13.35 g; 92.2 mmol) was added to a cooled solution of 9-benzyloxyadenine (14.9 g, 61.5 mmol), 4-dimethylaminopyridine (1.5 g, 12.3 mmol) and triethylamine (25.7 ml, 184.4 mmol) in tetrahydrofuran (200 ml). After 1 hour at room temperature the solvent was removed under reduced pressure and the residue partitioned between chloroform (500 ml) and saturated potassium bicarbonate (300 ml). The organic phase was separated, washed with water (200 ml), brine (200 ml), dried (MgSO$_4$) and evaporated to dryness. Column chromatography on silica gel eluting with chloroform-methanol (100:1) afforded the title compound (11.20 g, 49%). IR: $\nu_{max}$ (KBr) 3070, 1800, 1740, 1730, 1605, 1585, 1450 and 1410 cm$^{-1}$; $^1$H NMR $\delta_H$ [(CD$_3$)$_2$SO] 5.70(2H, s, CH$_2$Ph), 7.55(5H, s, CH$_2$Ph), 8.20(4H, s, Ar), 8.95(1H, s, H-2), 9.25(1H, s, H-8). Found: C, 64.71; H, 3.78; N, 18.85%; m/z 371.1025. C$_{20}$H$_{13}$N$_5$O$_3$ requires: C, 64.68; H, 3.54; N, 18.86%; m/e 371.1018.

d) 9-Hydroxy-6-phthalimidopurine

A mixture of 9-benzyloxy-6-phthalimidopurine (11.0 g, 29.5 mmol), 10% palladium on charcoal (2.2 g), ethanol (300 ml) and tetrahydrofuran (500 ml) was stirred at 25° C. for 1 hour under an atmosphere of hydrogen. The suspension was then filtered and the catalyst washed with ethanol. The filtrate was evaporated under reduced pressure and the resulting solid triturated with ether. The solid was collected and then dried to afford the title compound (6.93 g; 83%). IR: $\nu_{max}$ (KBr). 2607, 1794, 1735, 1603, 1582, 1467, 1401 cm$^{-1}$; $^1$H NMR $\delta_H$ [(CD$_3$)$_2$SO] 8.15(4H, s, Ar), 8.95(1H, s, H-2), 9.15(1H, s, H-8), 12.80(1H, br.s, D$_2$O exchangeable, OH). Found: C, 55.34; H, 2.58; N, 24.56%. C$_{13}$H$_7$N$_5$O$_3$ requires: C, 55.51; H, 2.51; N, 24.91%.

e) 9-[3-Acetoxy-2-(diethoxyphosphorylmethoxy)-propoxy]-6-N-phthalimidopurine

Diethyl azodicarboxylate (0.4 ml, 2.6 mmol) was added to a mixture of 9-hydroxy-6-N-phthalimidopurine (0.61 g, 2.17 mmol), diethyl [2-acetoxy-1-(hydroxymethyl)ethoxy]methylphosphonate (0.61 g, 2.17 mmol) triphenylphosphine (0.68 g, 2.6 mmol) in dry THF (20 ml) at 0° C. A pale yellow solution was obtained within a few minutes and the reaction mixture was then stirred at ambient temperature for 2 hours. The solvent was evaporated under reduced pressure and the residue obtained chromatographed on silica gel using hexane: acetone 3:1 as eluant, before changing to acetone: hexane 3:1 to give the title compound as a colourless oil (0.95 g, 80%). IR: $\nu_{max}$ (film) 3100, 3060, 2980, 2910, 1790, 1740, 1730, 1600, 1580, 1465, 1445, 1405, 1370, 1330, 1240, 1160, 1135, 1020, 980, 880, 790, 775 cm$^{-1}$. $^1$H NMR: $\delta_H$ [(CD$_3$)$_2$SO] 1.23 (2×3H, 2×t, J=7 Hz, (OCH$_2$CH$_3$)$_2$). 2.05 (3H,s, COCH$_3$), 3.95–4.45 (9H,m, OCH$_2$CH$_3$)$_2$+OCH$_2$P, CHCH$_2$OAc), 4.55–4.80 (2H,m, N-OCH$_2$), 8.0–8.20 (4H,m, aromatic H), 9.04 (1H,s) 9.11(1H,s). m/z: (FAB, thioglycerol matrix) 548 (MH$^+$, 100).

b) 9-[3-Acetoxy-2-(diethoxyphosphorylmethoxy)-propoxy]adenine

To a solution of 9-[3-acetoxy-2-(diethoxyphosphorylmethoxy)propoxy]-6-N-phthalimidopurine (0.91 g, 1.66 mmol) in dry dichloromethane (5 ml) was added methylhydrazine (0.09 ml, 1.1 eq) and the solution stirred at ambient temperature for 15 minutes. The reaction mixture was filtered, the white solid washed with dichloromethane and the combined filtrates evaporated to dryness. The residue obtained was chromatographed on silica gel (dichloromethane:methanol 95:5 as eluant) to give the title compound as a colourless oil (0.58 g, 83). IR: $\nu_{max}$ (film) 3330, 3190, 2990, 2900, 1740, 1660, 1640, 1595, 1470, 1410, 1370, 1330, 1295, 1240, 1050, 1020, 975, 820, 790 cm$^{-1}$. $^1$H NMR: $\delta_H$ [(CD$_3$)$_2$SO] 1.23 (2×3H, 2×t, J=7 Hz, (OCH$_2$CH$_3$)$_2$), 2.03 (3H,s, COCH$_3$), 4.0–4.15 (7H,m, (OCH$_2$CH$_3$)$_2$+OCH+OCH$_2$P), 4.15–4.3-7 (2H, 2xdd, J=12.10, 5.2, 4.1 Hz, C$_{20}$Ac), 4.44 (1H,dd, J=11.3 H$_z$,J=6.0 Hz,NOCH$_B$), 4.55 (1H, dd, J=11.27 Hz, J=3.85 Hz, NOCHA), 7.38 (2H,br.s,D$_2$O exchangeable NH$_2$), 8.15 (1H,s), 8.43(1H,s). Found: C,42.01; H,5.86; N,16.14%; C$_{15}$H$_{24}$N$_5$O$_7$P. 0.5H$_2$O. requires: C,42.25; H,5.91; N,16.42%. m/z: observed 417.1412; C$_{15}$H$_{24}$N$_5$O$_7$P requires: 417.1412.

DESCRIPTION 11

Intermediates for Examples 9 (Method B), 10, 15 and 20 a) 6-Benzyloxyamino-4-chloro-2,5-diformamidopyrimidine

A mixture of 4,6-dichloro-2,5-diformamido-pyrimidine (1.9 g, 8.09 mmol), benzyloxyamine (1 g, 8.13 mmol), triethylamine (2 ml) and dioxan (20 ml) was stirred at 100° C. for 1 hour. The cooled reaction mixture was filtered and the precipitate collected and washed with dioxan (2×5 ml). The filtrate and washings were combined and evaporated to a syrup. Column chromatography on silica gel (eluted with chloroform-ethanol, 30:1) afforded the title compound (1.2 g, 46%). IR: $\nu_{max}$ (KBr) 3242, 1694, 1588, 1472 cm$^{-1}$; $^1$H NMR $\delta_H$ [(CD$_3$)$_2$SO], 4.89 (2H, s, OCH$_2$Ph), 7.4 (5H, m, Ph), 8.15 (1H, s, CHO), 9.18, 9.42 (1H, 2×br.s, D$_2$O exchangeable, NH), 9.25 (1H, br.s, CHO), 10.91 (2H, br.s, D$_2$O exchangeable, 2×NH). m/z (FAB+ve ion, thioglycerol) MH$^+$322.

b) 9-Benzyloxy-6-chloro-2-formamidopurine

6-Benzyloxyamino-4-chloro-2,5-diformamidopyrimidine (1.2 g, 3.73 mmol) and diethoxymethyl acetate (20 ml) was stirred at 120° C. for 2.5 hours, cooled and evaporated under reduced pressure. A solution of the residue in methanol (20 ml) and 0.880 ammonia (2 ml) was stirred at 20° C. for 1 hour, the solvent removed under reduced pressure and the residue co-evaporated with methanol. Column chromatography on silica gel (eluted with chloroform-ethanol, 100:1) afforded the title compound (700 mg, 62%). IR: $\nu_{max}$ (KBr) 3119, 1702, 1611, 1577, 1505, 1440 cm$^{-1}$; $^1$H NMR: $\delta_H$ [(CD$_3$)$_2$SO], 5.44 (2H, s, CH$_2$Ph), 7.45 (5H, m, Ph), 8.54 (1H, s, H-8), 9.34 (1H, s, CHO), 11.30 (1H, br.s, D$_2$O exchangeable, NH). Found: C, 49.99; H, 3.37; N, 22.43%, m/z 303.0523. C$_{13}$H$_{10}$N$_5$O$_2$Cl+0.5 H$_2$O requires: C, 49.92; H, 3.55; N, 22.40%, m/z 303.0520.

c) 2-Amino-9-benzyloxy-6-methoxypurine

A mixture of 9-benzyloxy-6-chloro-2-formamidopurine (440 mg, 1.60 mmol), 1.2M sodium methoxide in methanol (5.3 ml) and methanol (10 ml) was heated at reflux temperature for 1 hour and then cooled. Acetic acid (4 ml) was added and the solution evaporated to dryness. The residue was suspended in water and extracted with chloroform (2×25 ml). The combined chloroform extracts were washed with brine, dried (magnesium sulphate) and evaporated under reduced pressure. Column chromatography on silica gel (eluted with chloroform-methanol, 100:1) afforded the title compound (331 mg, 76%). IR: $\nu_{max}$ (KBr) 3480, 3310, 1625, 1585, 1505, 1485, 1460, 1400 cm$^{-1}$; $^1$H NMR: $\delta_H$ [(CD$_3$)$_2$SO] 3.96 (3H, s, CH$_3$), 5.31 (2H, s, CH$_2$Ph), 6.64 (2H, br.s, D$_2$O exchangeable, NH$_2$), 7.42 (5H, s, Ph), 7.75 (1H, s, H-8). Found: C, 57.18, H, 4.84; N, 25.85%). m/z 271.1075. C$_{13}$H$_{13}$N$_5$O$_2$ requires: C, 57.56, H, 4.83, N, 25.82%; m/z 271.1069.

d) 9-Benzyloxy-2-(bis-t-butoxycarbonyl)amino]-6-methoxypurine

A solution of 2-amino-9-benzyloxy-6-methoxypurine (0.47 g; 1.73 mmol), di-t-butyldicarbonate (0.57 g; 2.60 mmol) and 4-N,N-dimethylaminopyridine (100 mg, 0.173 mmol) in tetrahydrofuran was heated at reflux for 45 minutes. Additional di-t-butyldicarbonate (0.20 g) was then added and the solution refluxed for 30 minutes. The reaction was then cooled and the solvent removed under reduced pressure. The residue was purified by column chormatography on silica gel eluting with chloroform-methanol mixtures, affording the title compound (740 mg; 91%). IR: $\nu_{max}$ (KBr) 3110, 2990, 1760, 1600, 1485, 1460, 1400 cm$^{-1}$; $^1$H NMR: $\delta_H$ (CDCl$_3$) 1.50(18H, s, 6×CH$_3$), 4.15(3H, S, CH$_3$), 5.45(2H, s, CH$_2$), 7.35(5H, s, Ar), 7.65(1H, s, H-8).

e) 2-[(Bis-t-butoxycarbonyl)amino}-9-hydroxy-6-methoxypurine

A mixture of 9-benzyloxy-2-[(bis-t-butoxycarbonyl)amino]-6-methoxypurine (990 mg; 2.10 mmol), 10% palladium on charcoal (100 mg), ethanol (25 ml) and dioxan (25 ml) was stirred at 20° C. under an atmosphere of hydrogen for 45 minutes. The suspension was then filtered and the filtrate evaporated under reduced pressure. The resulting white solid was dried to yield the title compound (760 mg; 95). IR: $\nu_{max}$ (KBr) 2990, 2420, 1760, 1740, 1730, 1710, 1605, 1480 cm$^{-1}$; $^1$H NMR $\delta_H$ [(CD$_3$)$_2$SO] 1.40(18H, s, 6×CH$_3$), 4.05(3H, s, OCH$_3$), 8.05(1H, s, H-8), 11.8(1H, br.s, D$_2$O exchangeable, OH) Found: C, 50.27; H, 6.12; N, 17.70%. C$_{16}$H$_{23}$N$_5$O$_6$+0.2EtOH requires: C, 50.42; H, 6.23; N, 17.66%.

f) 9-3-Acetoxy-2-(diethoxyphosphorylmethoxy)-propoxy]2-[bis-(t-butoxycarbonyl)amino-6-methoxypurine Diethyl azodicarboxylate (0.49 ml, 3.15 mmol) was added to a mixture of 2-[bis-(t-butoxycarbonyl)amino]-9-hydroxy-6-methoxypurine (1 g, 2.6 mmol) triphenylphosphine (0.82 g, 3.15 mmol) and diethyl [2-acetoxy-1-(hydroxymethyl)ethoxy]methylphosphonate (0.74 g, 2.6 mmol) in dry THF (20 ml) at 0° C. The reaction mixture was stirred at ambient temperature for 3 hours, the solvent removed under reduced pressure and the residue obtained chromatographed on silica gel (haxane:acetone 3:1 as eluant, then hexane:acetone 1:1 and finally hexane:acetone 1:3) to give the title compound as a colourless oil (1 g, 59%). IR: $\nu_{max}$ (film) 2980, 2940, 1790, 1740, 1595, 1490, 1425, 1370, 1280, 1250, 1165, 1120, 1100, 1050, 970, 850, 790 cm$^{-1}$. $^1$H NMR: $\delta_H$ [(CD$_3$)$_2$SO] 1.22 (2×3H, 2×t, J=7 Hz, (OCH$_2$CH$_3$)$_2$), 1.41 (18H,s, 2×C(CH$_3$)$_3$), 2.02 (3H,s, COCH$_3$), 3.75-4.40 (9H,m, (OCH$_2$CH$_3$)$_2$+OCH$_2$P+CHCH$_2$OAc), 4.08 (3H,s,OCH$_3$), 4.48 (1H, dd, J=6.05 Hz, J=11.27 Hz, NOCH$_B$), 4.58 (1H,dd,J=3.3 Hz, J=11.27 Hz, NOCHA), 8.76 (1H,s,H-8). m/z: (FAB, thioglycerol matrix) 648 (MH$^+$, 9%).

DESCRIPTION 12 a) (S)-1-Benzyloxy-3-(t-butyldiphenylsilyloxy)propan-2-ol

To a solution of (R)-3-benzyloxypropane-1,2-diol (prepared from (S)-4-benzylymethyl-2,2-dimethyl-1,3-dioxolane (commercially available from FLUKA) by acid hydrolysis using 80% aqueous acetic acid), (8.3 g, 47.2 mmol) in dry THF (70 ml) was added imidazole (6.42 g, 94.4 mmol). After 2 minutes, t-butyldiphenylsilyl chloride (12.28 ml, 47.2 mmol) was added. A white precipitate formed immediately. After 2 hours, the reaction mixture was filtered and the filtrate evaporated. The residue was partitioned between ethyl acetate and water, the organic layer separated, washed with saturated brine, dried (MgSO$_4$), filtered and evaporated to give a colourless oil. Chromatography of the oil on silica gel (dichloromethane as eluant) afforded the title compound as a colourless oil (17.72 g, 90%).

IR $\nu_{max}$ (film) 3580, 3070, 2940, 2860, 1595, 1475, 1455, 1430, 1395, 1365, 1345, 1310, 1270, 1265, 1240, 1110, 1030, 1010, 1000, 960, 940, 828, 810, 745, 710 cm$^{-1}$. $^1$H NMR: $\delta_H$ [(CD$_3$)$_2$SO] 0.97 (9H, s, t-Bu), 3.4-3.85 (5H, m, CH$_2$CHCH$_2$), 4.50 (2H, s, OCH$_2$Ph), 4.84 (1H, d, J=5.3 Hz, D$_2$O exchangeable OH), 7.25-7.70 (15H, m, aromatic H). Found C, 74.27, H, 7.71%. C$_{26}$H$_{32}$O$_3$Si requires: C, 74.24; H, 7.67%. m/z: (NH$_3$ C.I.) 438 (MNH$_4$+, 8%). [α]$_D^{25}$ (CHCl$_3$) −1.7° (C=0.94).

b) Diethyl (S)-[2-benzyloxy-1-(t-butyldiphenylsilyloxymethyl)ethoxy]methylphosphonate Dry HCl gas was bubbled through a solution of (S)-1-benzyloxy-3-(t-bttyldiphenylsilyloxy)propan-2-ol (4.206 g, 0.01 mmol) and paraformaldehyde (0.3 g, 0.01 mmol) in dry dichloromethane (20 ml) containing anhydrous calcium chloride (7.5 g), for 1 hour. Any remaining traces of water were removed by drying over magnesium sulphate. The solution was filtered and evaporated to dryness to give a colourless oil. Triethyl phosphite (1.71 ml, 0.01 mmol) was added and the solution was heated at 140° C. for 5 hours, then allowed to cool to ambient temperature. The reaction product was chromatographed on silica gel (dichloromethane: methanol, 99:1 as eluant) to give the title compound as a colourless oil (2.25 g, 40%).

IR: $\nu_{max}$ (film) 3060, 2960, 2930, 2900, 2850, 1475, 1455, 1430, 1390, 1365, 1260, 1115, 1055, 1030, 960, 820, 805, 740, 710 cm$^{-1}$. 1H NMR: $\delta_H$ (CDCl$_3$) 1.03 (9H, s, t-Bu), 1.28 (2×3H, 2×t, J=7 Hz, (OCH$_2$CH$_3$)$_2$), 3.5-3.85 (5H, m, CH$_2$CHCH$_2$), 3.96 (2H, d, J=8.9 Hz, OCH$_2$P), 4.05-4.25 (4H, m, (OCH$_2$CH$_3$)$_2$), 4.52 (2H, s, OCH$_2$Ph), 7.25-7.75 (15H, m, aromatic H). Found: C, 65.43; H, 7.70%. C$_{31}$H$_{43}$O$_6$PSi requires: C, 65.24; H, 7.59%. m/z: (NH$_3$ C.I.) 588 (MNH$_4$+, 35%), 571 (MH+, 100%). [α]D$^{25}$ (CHCl$_3$) −6.9° (C=1.06).

DESCRIPTION 13 [(R)-ISOMERS]

Diethyl (S)-[1-(t-butyldiphenylsilyloxymethyl)-2-hydroxyethoxy]methylphosphonate To a solution of diethyl (S)-[2-benzyloxy-1-(t-butyldiphenylsilyloxymethyl)ethoxy]methylphosphonate (1.90 g, 3.3 mmol) in ethanol (20 ml) containing a trace of methanol/HCl (10 drops), was added 10%Pd-C (1.2 g).

The mixture was shaken under an atmosphere of hydrogen at ambient temperature and atmospheric pressure until hydrogen uptake was complete and t.l.c. (SiO$_2$, CH$_2$Cl$_2$-MeOH, 95:5) indicated no starting material remained. The reaction mixture was filtered, the filtrate evaporated and the residue obtained chromatographed on silica gel (dichloromethanemethanol, 95:5 as eluant) to give the title compound as a colourless oil (1.35 g, 84%).

IR: $\nu_{max}$ (film) 3420, 3080, 3060, 2945, 2870, 1595, 1475, 1430, 1395, 1365, 1245, 1115, 1060, 1030, 975, 825, 745, 715 cm$^{-1}$. $^1$H NMR: $\delta_H$ [(CD$_3$)$_2$SO]1.0 (9H, s, t-Bu), 1.20 (2×3H, 2×t, J=7.1 Hz, (OCH$_2$CH$_3$)$_2$), 3.45–3.60 (3H, m, CH$_2$CH), 3.65–3.80 (2H, m, CH$_2$), 3.90–4.15 (6H, m, OCH$_2$P,(OCH$_2$CH$_3$)$_2$), 4.65 (1H, t, J=5.2 Hz, D$_2$O exchangeable OH), 7.30–7.75 (10H, m, aromatic H). Found: C, 60.11; H, 7.87%.C$_{24}$H$_{37}$O$_6$PSi requires: C, 59.97; H, 7.76%. m/z: (NH$_3$ C.I.) 498 (MNH$_4^+$, 15%), 481 (MH$^+$, 100%). [α]D$^{25}$ (CHCl$_3$) −19.0° (C=0.4).

DESCRIPTION 14 [(S)-ISOMERS]

Diethyl (R)-[2-benzyloxy-1-(hydroxymethyl)ethoxy]-methylphosphonate

A suspension of diethyl (S)-[2-benzyloxy-1-(t-butyldiphenylsilyloxymethyl)ethoxy]methylphosphonate (3.09 g, 5.4 mmol) in trifluoroacetic acid/water 2:1 (12 ml) was stirred at ambient temperature for 1 hour. The solution obtained was extracted with hexane (2×10 ml) and the aqueous containing phase evaporated to dryness. The residue obtained was treated with ethanolic ammonia (5 ml) for 5 minutes at ambient temperature, the solvent evaporated and the residue chromatographed on silica gel using dichloromethane/methanol 95:5 as eluant. The title compound was obtained as a colourless oil (1.35 g, 75%). IR: $\nu_{max}$ (film) 3380, 3060, 3030, 2980, 2910, 2860, 1495, 1480, 1450, 1390, 1370, 1250, 1160, 1100, 1075, 975, 910, 890, 820, 780, 740, 700 cm$^{-1}$. $^1$H NMR: $\delta_H$[(CD$_3$)$_2$SO]1.21, 1.22 (2×3H, 2×t, J=7 Hz, (OCH$_2$CH$_3$)$_2$, 3.4–3.65 (5H, m, CH$_2$, CH,CH$_2$), 3.94 (2H, d, J=8.5 Hz, OCH$_2$P), 3.97–4.1 (4H, m, (OCH$_2$CH$_3$)$_2$), 4.5 (2H, s, CH$_2$Ph), 4.67 (1H, t, J=5.5 Hz, D$_2$O exchangeable OH), 7.20–7.40 (5H, m, Ph). Found: C, 53.20; H, 7.72%. C$_{15}$H$_{25}$O$_6$P 0.33 H$_2$O requires: C, 53.25; H, 7.64%. m/z: observed 332.1383. C$_{15}$H$_{25}$O$_6$P requires 332.1387. [α]D$^{25}$ (CHCl$_3$) +16.7° (c=1.06).

EXAMPLES

Compounds of formula (I) prepared as hereinbefore described [R$_3$/R$_4$ when joined—see formula (I)].

| Ex. No. | R$_1$ | R$_2$ | R$_3$ | R$_4$ | |
|---|---|---|---|---|---|
| 1 | NH$_2$ | H | H | P(O)(OEt)$_2$ | |
| 2 | NH$_2$ | H | H | P(O)(OH)$_2$ | |
| 3 | OH | NH$_2$ | H | P(O)(OEt)$_2$ | |
| 4 | OH | NH$_2$ | H | P(O)(OH)$_2$ | |
| 5 | OH | NH$_2$ | H | P(O)(OH)(OEt) | |
| 6 | NH$_2$ | H | CH$_2$OH | P(O)(OEt)$_2$ | |
| 7 | NH$_2$ | H | CH$_2$OH | P(O)(OH)$_2$ | |
| 8 | NH$_2$ | H | CH$_2$OH | P(O)(OH)(OEt) | |
| 9 | OH | NH$_2$ | CH$_2$OH | P(O)(OEt)$_2$ | |
| 10 | OH | NH$_2$ | CH$_2$OH | P(O)(OH)$_2$ | |
| 11 | NH$_2$ | NH$_2$ | H | P(O)(OEt)$_2$ | |
| 12 | NH$_2$ | NH$_2$ | H | P(O)(OH)$_2$ | |
| 13 | Cl | NH$_2$ | H | P(O)(OH)$_2$ | |
| 14 | OCH$_3$ | NH$_2$ | H | P(O)(OH)$_2$ | |
| 15 | OH | NH$_2$ | joined (R$_6$ = H) | | |
| 16 | NH$_2$ | NH$_2$ | CH$_2$OH | P(O)(OH)$_2$ | |
| 17 | OH | NH$_2$ | CH$_2$OH | P(O)(OH)$_2$ | (R)-isomer |
| 18 | OH | NH$_2$ | joined (R$_6$ = H) | | (S)-isomer |
| 19 | NH$_2$ | H | CH$_2$OH | P(O)(OH)$_2$ | (R)-isomer |
| 20 | OH | NH$_2$ | CH$_2$OH | P(O)(OH)$_2$ | (S)-isomer |
| 21 | OH | NH$_2$ | joined (R$_6$ = H) | | (R)-isomer |
| 22 | NH$_2$ | H | CH$_2$OH | P(O)(OH)$_2$ | (S)-isomer |
| 23 | NH$_2$ | NH$_2$ | CH$_2$OH | P(O)(OH)$_2$ | (R)/(S)-isomers |
| 24 | NH$_2$ | H | joined (R$_6$ = H) | | (R)/(S)-isomers |
| 25 | NH$_2$ | NH$_2$ | joined (R$_6$ = H) | | (R)/(S)-isomers |

EXAMPLE 1

9-[2-(Diethoxyphosphorylmethoxy)ethoxy]adenine

A solution of 6-chloro-9-[2-(diethoxyphosphorylmethoxy)ethoxy]purine (1.45 g, 4 mmol) in ethanol (20 ml) saturated with ammonia gas was heated in a sealed steel vessel at 100° C. for 2 hours. The reaction mixture was cooled to ambient temperature, evaporated to dryness and the residual oil chromatographed on silica gel (eluted with dichloromethane: methanol, 90:10) to give recovered starting material (0.25 g) and the title compound (0.94 g, 82%—based on used starting material), crystallised from acetone-ether, m.p. 74°–76°. UV: $\lambda_{max}$ (EtOH) 260 nm (ε 13,500); IR: $\nu_{max}$ (KBr) 3308, 3146, 1669, 1646, 1600, 1538, 1466, 1416, 1320, 1301, 1232, 1206, 1164, 1129. 1066, 1053, 1039, 1009, 978 cm$^{-1}$; $^1$H NMR: $\delta_H$ [(CD$_3$)$_2$SO]1.24 (6H,t,J=7 Hz, (OCH$_2$CH$_3$)$_2$), 3.83–3.89 (2H,m,CH$_2$OCH$_2$P), 3.91 (2H,d,J=8 Hz, OCH$_2$P), 4.0–4.15 (4H, dq, J=7 Hz, 7 Hz, (OCH$_2$CH$_3$)$_2$), 4.48–4.51 (2H,m,N-OCH$_2$), 7.37 (2H,br.s,D$_2$O exchangeable NH$_2$), 8.14 (1H,s,H-8), 8.34 (1H,s,H-2). Found: C,41.74; H: 5.49; N: 20.06%; m/z 345.1202. C$_{12}$H$_{20}$N$_5$O$_5$P requires: C,41.74; H, 5.83; N, 20.28%; m/z 345.1212.

EXAMPLE 2

9-[2-(Phosphonomethoxy)ethoxy]adenine

To a solution of 9-[2-(diethoxyphosphorylmethoxy)ethoxy]adenine (0.63 g, 1.83 mmol) in dry dichloromethane (10 ml) was added trimethylsilyl bromide (1.45 ml, 11 mmol) and the solution stirred at ambient temperature for 2 hours. The solvent was removed under reduced pressure and the residue dissolved in methanol (10 ml). The solvent was evaporated and the residue again dissolved in methanol and solvent evaporated to give a solid residue. Crystallisation from methanol: acetone gave the title compound which was recrystallised from methanol: water (0.24 g, 45%), m.p. 241°-244° C. UV: $\lambda_{max}$ (EtOH) 259 nm ($\epsilon$ 13,500); IR: $\nu_{max}$ (KBr) 3428, 3312, 3084, 1685, 1644, 1612, 1484, 1462, 1455, 1336, 1294, 1278, 1255, 1215, 1195, 1104, 1060, 1046, 1033, 955, 934, 892 cm$^{-1}$. $^1$H NMR: $\delta$H [(CD$_3$)$_2$SO]3.64 (2H,d,J=8.2 Hz, OCH$_2$P), 3.82 (2H,m,N-OCH$_2$CH$_2$O), 4.50 (2H,m, N-OCH$_2$CH$_2$), 7.42 (2H, br.s, D$_2$O exchangeable NH$_2$), 8.15 (1H,s,H-8), 8.38 (1H,s,H-2) 10.0–4.5 (2H,broad, D$_2$O exchangeable PO(OH )$_2$). Found: C,32.84; H,4.41; N: 23.74%. C$_8$H$_{12}$N$_5$O$_5$P. H$_2$O requires: C,33.01; H,4.19; N:24.06%.

EXAMPLE 3

9-[2-(Diethoxyphosphorylmethoxy)ethoxy]quanine

A solution of 6-chloro-9-[2-(diethoxyphosphorylmethoxy)ethoxy]-2-formamidopurine (2.1 g, 5.1 mmol) in 80% aqueous formic acid (15 ml) was stirred and heated at 80° C. for 1.5 hours. After cooling to ambient temperature, the reaction mixture was evaporated to dryness under reduced pressure, the residue dissolved in methanol (20 ml) and .880 ammonia (2 ml) and left at ambient temperature for 1 hour. The solvent was evaporated and the residue obtained chromatographed on silica gel (eluted with dichloromethane: methanol, 90:10) to give the title compound (1.5 g, 80%), which was crystallised from ethanol (0.8 g, 43%) m.p. 176°-178°. UV: $\nu_{max}$ (H$_2$O) 253 ($\epsilon$ 13,300)nm; $\lambda_{sh}$ (H$_2$O) 275 ($\epsilon$ 9050)nm; IR: $\nu_{max}$ (KBr) 3334, 3156, 1693, 1646, 1601, 1590, 1242, 1163, 1054, 1025, 970 cm$^{-1}$; $^1$H NMR: $\delta_H$ [(CD$_3$)$_2$SO]1.24 (6H,t,J=7 Hz, (OCH$_2$CH$_3$)$_2$), 3.80 (2H,m, N-OCH$_2$CH$_2$O), 3.90 (2H,d,J=8 Hz, OCH$_2$P), 4.06 (4H,dq,J=7 Hz,7 Hz, (OCH$_2$CH$_3$)$_2$), 4.39 (2H,m, N-OCH$_2$CH$_2$), 6.60 (2H,br.s, D$_2$O exchangeable, NH$_2$), 7.89 (1H,s,H-8), 10.67 (1H,br.s, D$_2$O exchangeable N-1(H)). Found: C,39.45; H,5.47; N,19.05%. C$_{12}$H$_{20}$N$_5$O$_6$P requires: C,39.89; H,5.58; N,19.39%.

EXAMPLE 4

9-[2-(Phosphonomethoxy)ethoxy]quanine

Method A

To a solution of 9-[2-(diethoxyphosphorylmethoxy)ethoxy]quanine (100 mg, 0.28 mmol) in dry dimethylformamide (2 ml) was added trimethylsilyl bromide (0.22 ml, 1.66 mmol). The reaction mixture was stirred for 16 hours at ambient temperature, evaporated to dryness and the residue obtained dissolved in methanol (5 ml). After 5 minutes at ambient temperature, the methanol was removed by evaporation. The residue was again treated with methanol as indicated above. The solid obtained was insoluble in water and methanol. This solid was suspended in water and 0.880 ammonia added until the solution pH reached 9-10. The basic solution was added to Dowex 50W-X8 resin (prewashed with 0.1M sodium hydroxide and then water until the washings were neutral) and the resin washed with water. Fractions containing UV absorbing material were combined and acidified with 2M HCl to precipitate a solid. The precipitate was collected and triturated with methanol to give the title compound as a white solid (50 mg, 60%), m.p. 275°-278° C. UV: $\nu_{max}$ (EtOH) 254nm ($\epsilon$ 10800); $\lambda_{sh}$ (EtOH) 278 nm ($\epsilon$ 6400); IR: $\nu_{max}$(KBr) 3378, 3161, 1705, 1649, 1602, 1459, 1382, cm$^{-1}$; $^1$H NMR: $\delta_H$[(CD$_3$)$_2$SO] 3.60 (2H,d,J=8.25 Hz, OCH$_2$P), 3.77 (2H,m,-CH$_2$OCH$_2$P), 4.37 (2H,m, N-OCH$_2$CH$_2$), 6.63(2H,br.s, D$_2$O exchangeable NH$_2$), 7.92 (1H,s,H-8); 10.67 (1H,br.s,D$_2$O exchangeable NH), 2.6–5.5 (2H,broad, phosphonic acid H). Found: C,30.79; H,4.24; N,21.96%. C$_8$H$_{12}$N$_5$O$_6$P. 0.5H$_2$O requires: C,30.59; H,4.17; N,22.30%.

Method B

To a solution of 6-chloro-9-[2-(diethoxyphosphorylmethoxy)ethoxy]-2-formamidopurine (0.25 g, 0.61 mmol) in methanol (5 ml), was added sodium methoxide solution (30 wt % in methanol; 0.5 ml, 2.62 mmol). The mixture was stirred and heated at 50° C. for 4 hours. After cooling to ambient temperature, 80% aqueous acetic acid (0.5 ml) was added to give a solution of pH6. The solution was evaporated to dryness and the residue partitioned between dichloromethane (10 ml) and aqueous sodium bicarbonate solution (10 ml). The aqueous phase was washed with dichloromethane (2×10 ml), the combined organic extracts dried (magnesium sulphate), and evaporated to dryness under reduced pressure. The residue obtained was chromatographed on silica gel (eluant dichloromethane: methanol 90:10) to give a 2-amino-6-methoxypurine derivative (0.20 g) which was used without any further purification. The chromatographed material (0.20 g) was dissolved in dichloromethane (2 ml), trimethylsilyl bromide (0.7 ml, 5.3 mmol) added, and the solution left at ambient temperature for 2 days. The solvent was evaporated under reduced pressure and the residue obtained co-evaporated with methanol (×2) to leave a white solid which crystallised from hot water giving the title compound as a white solid (0.105 g, 56%) m.p. 275°-278° C., identical in all respects with the compound obtained in Method A.

EXAMPLE 5

9-[2-[Ethoxy(hydroxy)phosphorylmethoxy)ethoxy]-quanine

A solution of 9-[2-(diethoxyphosphorylmethoxy)ethoxy]quanine (100 mg, 0.28 mmol) in 10% (w/w) sodium hydroxide solution (3 ml) was heated under reflux for 4 hours. After cooling to ambient temperature, the solution was neutralised with 12M HCl and evaporated to dryness to give a yellow solid. The solid was purified by chromatography on reverse phase silica eluting initially with water, then methanol-water (5:95) and finally methanol-water (10:90). UV absorbing fractions were collected and evaporated to dryness to leave the title compound as a white solid, m.p. 244°-246° (25 mg, 27%).$^1$H NMR: 67 H [(CD$_3$)$_2$SO+C$_5$D$_5$D] 1.18 (3H, t, J=7 Hz, OCH$_2$CH$_3$), 3.74 (2H, d, J=8.5 Hz, OCH$_2$P), 3.80–3.85 (2H, m, CH$_2$OCH$_2$P), 3.98 (2H, m, P-OCH$_2$CH$_3$), 4.40–4.45 (2H, m, N-OCH$_2$), 7.07 (2H, br.s, D$_2$O exchangeable, NH$_2$), 8.01 (1H, s, H-8), 11.40 (1H, br.s, D$_2$O exchangeable, NH), 4.1–4.7 (br.s, P-OH+water in solvent). Found: C, 35.34; H, 4.78; N, 20.40%. C$_{10}$H$_{16}$N$_5$O$_6$P. 0.5H$_2$O requires: C, 35.09; H, 5.00; N, 20.46%.

EXAMPLE 6

9-[2-(Diethoxyphosphorylmethoxy)-3-hydroxypropoxy]adenine

Method A

A solution of 9-[3-acetoxy-2-(diethoxyphosphorylmethoxy)propoxy]adenine (0.58 g, 1.39 mmol) in ethanol (10 ml) and 2MHCl (1.5 ml, 3.0 mmol) was heated under reflux for 16 hours. The solution was cooled to ambient temperature and evaporated to dryness. The residue obtained was dissolved in ethanol and 0.880 ammonia solution added to give a final solution of pH 8.5. The solvent was removed under reduced pressure and the residue obtained chromatographed on silica gel (eluant dichloromethane:methanol 95:5, then 92:8, and finally 90:10) to give the title compound as a pale yellow oil (0.42 g, 80%). $^1$H NMR: $\delta_H$[(CD$_3$)$_2$SO] 1.23 (6H,t,J=7 Hz, (OCH$_2$CH$_3$)$_2$), 3.57 (2H,m, CH$_2$OH), 3.79 (1H,m,CH), 3.95–4.15 (6H,m, OCH$_2$P, (OCH$_2$CH$_3$)$_2$), 4.38 (1H,dd.J=6.6 Hz, J=11.27 Hz, NOCH$_B$), 4.54 (1H,dd,J=3.03 Hz, J=11.27 Hz, NOCH$_A$), 4.88 (1H,t, D$_2$O exchangeable OH), 7.38 (2H,br.s,D$_2$O exchangeable NH$_2$), 8.15 (1H,s), 8.43 (1H,s). Found: C,38.72; H,6.06; N,17.50%; C$_{13}$H$_{22}$N$_5$O$_6$P.1.5H$_2$O requires: C,38.80; H,6.01; N,17.41%. m/z: observed: 375.1306; C$_{13}$H$_{22}$N$_5$O$_6$P(M+) requires: 375.1308.

Method B

To a solution of 9-[3-benzyloxy-2-(diethoxyphosphorylmethoxy)propoxy]adenine (300 mg, 0.65 mmol) in 80% aqueous acetic acid (10 ml) was added 10% Pd-C (30 mg) and the mixture shaken under a hydrogen atmosphere at ambient temperature and pressure for a total of 8 hours. The solution was filtered and the filtrate evaporated. The residue obtained was chromatographed on silica (dichloromethane/methanol 95:5, then 90:10 as eluants) to give the title compound, (100 mg, 40%).

Method C

A solution of 9-[3-acetoxy-2-(diethoxyphosphorylmethoxy)propoxy]-6-chloropurine (0.63 g, 1.44 mmol) in ethanolic ammonia (12 ml) was heated in a sealed vessel at 100° C. for 5 hours. After cooling to ambient temperature, the solvent was removed under reduced pressure to leave a brown solid. The solid was chromatographed on silica gel (dichloromethane:methanol 90:10 as eluant) and separated into 9-[3-acetoxy-2-(diethoxyphosphorylmethoxy)propoxy]adenine (0.29 g) and 9-[2-(diethoxyphosphorylmethoxy)-3-hydroxypropoxy]adenine. The acetate derivative was hydrolysed as in Method A, and the product of the hydrolysis combined with the initially chromatographed alcohol to give the title compound as a pale yellow oil (0.30 g, 55%).

EXAMPLE 7

9-[3-Hydroxy-2-(phosphonomethoxy)propoxy]adenine and

EXAMPLE 8

9-[2-[ethoxy(hydroxy)phosphorylmethoxy]-3-hydroxypropoxy]adenine

To a solution of 9-[2-(diethoxyphosphorylmethoxy)-3-hydroxypropoxy]adenine (90 mg, 0.24 mmol) in dry dichloromethane (2.5 ml) and dry DMF (0.5 ml), was added bromotrimethylsilane (0.19 ml, 1.44 mmol). After 2 hours stirring at ambient temperature, the solvent was evaporated and the residue obtained dissolved in methanol. The solution was evaporated to dryness again and the residue again dissolved in methanol and evaporated. The residue was chromatographed on reverse phase silica [water (2 column volumes), then 5% methanol:water (3 column volumes), then 10% methanol: water (3 column volumes) as eluents] to give the diacid (17 mg, 22%), mp 197°–203°, and the monoacid-monoester (30 mg, 36%) mp 90°–95°, after lyophilisation.

Data for diacid, (Example 7), IR: $\nu_{max}$ (KBr disc) 3550–2100 (broad), 1704, 1608, 1467, 1418, 1340, 1304, 1229, 1207, 1163, 1125, 1079, 925, 889, 778, 757, 730 cm$^{-1}$. $^1$H NMR: $\delta_H$ [(CD$_3$)$_2$SO] 3.54 (2H, m, CHCH$_2$OH), 3.75 (3H, m, OCH$_2$P +CH$_2$CHCH$_2$), 4.3–4.56 (2H, m, N-OCH$_2$), 7.39 (2H, br.s, D$_2$O exchangeable NH$_2$), 8.15 (1H, s), 8.48 (1H, s), 3.45 (3H, br.s, D$_2$O exchangeable PO(OH)$_2$+CH$_2$OH) UV: $\lambda_{max}$ (EtOH) 259 nm. Found: C, 31.02; H, 4.50; N, 19.85%. C$_9$H$_{14}$N$_5$O$_5$P. 1.5H$_2$O requires: C, 31.22; H, 4.94; N, 20.23%. m/z: (FAB. thioglycerol matrix) 320 (MH+).

Data for monoester, (Example 8). IR: $\nu_{max}$ (KBr) 3600–2200 (broad), 1692, 1647, 1602, 1472, 1413, 1333, 1296, 1166, 1128, 1047, 953, 882, 795, 781, 729. UV: $\nu$max (EtOH) 259 nm. $^1$H NMR: $\delta_H$ [(CD$_3$)$_2$SO] 1.9 (3H, t, J=7 Hz, P-(OCH$_2$CH$_3$), 3.54 (2H, m, CHCH$_2$OH), 3.74 (1H, m, CHCH$_2$OH) 3.83 (2H, d, J=8.8 Hz, OCH$_2$P), 3.96 (2H, m, P-OCH$_2$CH$_3$), 4.3–4.55(2H, m, N-OCH$_2$), 7.39 (2H, br.s, D$_2$O exchangeable NH$_2$), 8.15 (1H, s), 8.46 (1H, s), 3.4 (2H, br.s, D$_2$O exchangeable P-OH+CH$_2$OH). Found: C, 37.10; H, 5.29; N, 19.59%. C$_{11}$H$_{18}$N$_5$O$_6$P. 0.5 1 H$_2$O requires: C, 37.08; H, 5.37; N, 19.65%. m/z: (FAB: thioglycerol matrix) 348 (MH+).

EXAMPLE 9

9-2-(Diethoxyphosphorylmethoxy)-3-hydroxypropoxy]quanine

Method A

A mixture of 9-[3-benzyloxy-2-(diethoxyphosphorylmethoxy)propoxy]quanine (300 mg, 0.6 mmol) and 5% Pd-C (30 mg) in 80% aqueous acetic acid (10 ml) was shaken under a hydrogen atmosphere at ambient temperature and pressure until hydrogen uptake had ceased—a total of 16 hours. The hydrogenation mixture was filtered and the filtrate evaporated. The residue was chromatographed on silica gel (dichloromethane/methanol 85:15 as eluant) to give the title compound as a white solid (84 mg, 30%) mp. 129°–133°. IR:$\nu_{max}$(KBr) 3335, 3150, 2984, 2933, 1693, 1648, 1602, 1476, 1382, 1244, 1164, 1116, 1053, 1026, 972 cm$^{-1}$. $^1$H NMR: $\delta_H$ [(CD$_3$)$_2$SO] 1.23 (6H, t, J=7 Hz, (OCH$_2$CH$_3$)$_2$), 3.45–3.65 (2H, m, CH$_2$OH), 3.7–3.85 (1H, m, CH$_2$CHCH$_2$), 3.9–4.2 (6H, m, (OCH$_2$CH$_3$)$_2$+OCH$_2$P), 4.2–4.5 (2H, m, N-OCH$_2$CH), 4.84 (1H, t, J=5.5 Hz, D$_2$O exchangeable OH), 6.6 (2H, s, D$_2$O exchangeable NH$_2$), 7.96 (1H, s, H-8), 10.69 (1H, br.s, D$_2$O exchangeable NH). Found; C, 39.15; H, 5.50; N, 17.14%. C$_{13}$H$_{22}$N$_5$O$_7$P. 0.5H$_2$O requires C, 39.00; H, 5.79; N, 17.49%. m/z: (positive ion FAB) 392 (M+H+).

Method B

A solution of 9-[3-acetoxy-2-(diethoxyphosphorylmethoxy)propoxy]-2-[bis-t-butoxycarbonyl)amino]-6-methoxypurine (0.28 g) 0.43 mmol) in ethanol (4 ml) and 2MHCl (1 ml) was heated under reflux for 5 hours. The solution was cooled and evaporated to dryness. The residue obtained was chromatographed on silica gel (pre-absorbed onto silica gel in ethanol; dichloromethane:methanol 80:20 as eluant) to afford 9-[2-(diethoxyphosphorylmethoxy)-3-hydroxypropoxy]quanine as a pale yellow solid (0.08 g, 47%).

EXAMPLE 10

9-[3-Hydroxy-2-(phosphonomethoxy)propoxy]quanine

To a solution of 9-[2-(diethoxyphosphorylmethoxy)-3-hydroxypropoxy]quanine (60 mg, 0.15 mmol) in dry dimethylformamide (1 ml) was added bromotrimethylsilane (0.5 ml, 3.75 mmol). The solution was kept at ambient temperature for 3 hours after which the solution was evaporated to dryness under reduced pressure. The residue obtained was dissolved in methanol and the solution evaporated to dryness again to leave an off-white solid. This solid was triturated with methanol to give the title compound as a white solid, m.p. >300°, (34 mg, 66%). IR $\nu_{max}$ (KBr). 3385, 3159, 1715, 1645. 1598, 1384, 1157. 1109, 1060, 930, 772 cm$^{-1}$. $^1$H NMR: $\delta_H$ [(CD$_3$)$_2$SO], 3.52 (2H, m, CH$_2$OH), 3.60–3.80 (3H, m, OCH$_2$P+CH$_2$CH) 4.25 (1H, dd, J=11 Hz, J=7.1 Hz, N-OCH$_B$), 4.40 (1H, dd, J=11 Hz, J=3.3 Hz N-OCH$_A$), 6.61 (2H, br.s, D$_2$O exchangeable NH$_2$), 8.00 (1H, s, H-8), 10.65 (1H, br.s, D$_2$O exchangeable NH) 2.6–4.1 (3H, broad, D$_2$O exchangeable OH, PO(OH)$_2$). Found: C, 31.59; H, 4.11; N, 20.42%. C$_9$H$_{14}$N$_5$O$_7$P. 0.25H$_2$O requires: C, 31.81, H, 4.27; N, 20.61%. m/z: (positive ion FAB) 336 (M+H$^+$).

EXAMPLE 11

2,6-Diamino-9-[2-(diethoxyphosphorylmethoxy)ethoxy]purine

A solution of 6-chloro-9-[2-(diethoxyphosphorylmethoxy)ethoxy]-2-formamidopurine (0.80 g, 1.96 mmol) in ethanol (10 ml) saturated with ammonia gas was heated in a sealed steel vessel at 110° C. for 5½ hours. The reaction mixture was cooled to ambient temperature, evaporated to dryness and the residue chromatographed on silica gel (eluted with dichloromethane:methanol 90:10) to give the title compound (0.25 g, 35%), m.p. 139°–141° (acetonitrile). UV: $\nu_{max}$ (EtOH) 256 ($\epsilon$8,200), 280 ($\epsilon$10,200)nm:

IR: $\nu_{max}$ (KBr) 3443, 3404, 3320, 3152, 2984, 2940, 1662, 1644, 1608, 1586, 1505, 1480, 1414, 1403, 1360, 1338, 1277, 1265, 1241, 1229, 1221, 1187, 1163, 1113, 1098, 1052, 1024, 978, 881, 842, 789, 769, 750 cm$^{-1}$. $^1$H NMR: $\delta_H$[(CD$_3$)$_2$SO] 1.24 (6H, t, J=7 Hz, (OCH$_2$CH$_3$)$_2$), 3.81 (2H, m, CH$_2$), 3.92 (2H, d, J=7.98 Hz, OCH$_2$P), 4.06 (4H, m, (OCH$_2$CH$_3$)$_2$), 4.38 (2H, m, N-OCH$_2$), 5.93 (2H, br.s, D$_2$O exchangeable NH$_2$), 6.79 (2H, br.s, D$_2$O exchangeable NH$_2$), 7.88 (1H, s, H-8).

Found: C,39.57; H,5.82; N,23.27%; C$_{12}$H$_{21}$N$_6$O$_5$P. 0.1 H$_2$O requires C,39.80; H,5.90; N,23.21%. m/z: observed 360.1318; C$_{12}$H$_{21}$N$_6$O$_5$P(M$^+$) requires 360.1312.

EXAMPLE 12

2,6-Diamino-9-[2-phosphonomethoxy)ethoxy]purine

To a solution of 2,6-diamino-9-[2-(diethoxyphosphorylmethoxy)ethoxy]purine (0.15 g, 0.41 mmol) in dry dichloromethane (3 ml) and dry dimethylformamide (1 ml) was added trimethylsilyl bromide (0.55 ml, 4.1 mmol) and the solution stirred at ambient temperature for 2 hours. The solvent was removed under reduced pressure and the residue dissolved in methanol. The solution was evaporated to dryness and the solid residue obtained triturated with methanol to give the title compound (75 mg, 59%) m.p. >300°. IR: $\nu_{max}$ (KBr) 3369, 3145, 3138, 3120, 1658, 1617, 1593, 1532, 1485, 1455, 1419, 1405, 1368, 1285, 1232, 1163, 1118, 1059, 915, 886, 841, 781, 766, 741, 716 cm$^{-1}$. $^1$H NMR: $\delta_H$ [(CD$_3$)$_2$SO] 3.60 (2H, d, J=8.25 Hz, OCH$_2$P), 3.75 (2H, m, CH$_2$), 4.37 (2H, m, NOCH$_2$), 6.0 (2H, br.s, D$_2$O exchangeable NH$_2$), 6.82 (2H, br.s, D$_2$O exchangeable NH$_2$), 7.93 (1H, s, H-8), 2.5–5.0 (broad, D$_2$O exchangeable PO(OH)$_2$+water from solvent). Found: C,30.28; H,4.81; N,26.03%. C$_8$H$_{13}$N$_6$O$_5$P. 0.9H$_2$O requires; C,29.99; H,4.65; N,26.23%.

EXAMPLE 13

2-Amino-6-chloro-9-[2-(phosphonomethoxy)ethoxy]purine

To a solution of 6-chloro-9-[2-(diethoxyphosphorylmethoxy)ethoxy]-2-formamidopurine (0.370 g, 0.91 mmol) in dry dimethylformamide (5 ml) was added trimethylsilyl bromide (1.3 ml, 9.6 mmol) and the solution stirred at ambient temperature for 3 hours. The solvent was removed under reduced pressure and the residue co-evaporated with acetone:water 1:1 (×2). The solid residue obtained was crystallised from hot water to give the title compound as a tan solid (0.15 g, 51%), m.p. 190°–195° C. IR: $\nu_{max}$ (KBr) 3480, 3430, 3200, 3150, 2920, 1660, 1625, 1570, 1525, 1480, 1370, 1320, 1235, 1195, 1125, 1105, 1030, 995, 950, 920, 880, 780 cm$^{-1}$. $^1$H NMR: $\delta_H$ [(CD$_3$)$_2$SO] 3.63 (2H, d, J=8.52 Hz, OCH$_2$P), 3.81 (2H, m, CH$_2$OCH$_2$P), 4.45 (2H, m, N-OCH$_2$), 2.75–5.25 (2H, broad, D$_2$O exchangeable PO(OH)$_2$), 7.11 (2H, br.s, D$_2$O exchangeable NH$_2$), 8.37 (1H, s, H-8). Found: C,28.89; H,3.51; N,21.15%. C$_8$H$_{11}$N$_5$O$_5$PCl. 0.5H$_2$O requires: C,28.88; H,3.63; N,21.06%.

m/z: (FAB, thioglycerol matrix) 324 (MH$^+$, 100%).

EXAMPLE 14

2-Amino-6-methoxy-9-[2-(phosphonomethoxy)ethoxy]purine

To a solution of 6-chloro-9-[2-(phosphonomethoxy)ethoxy]quanine (0.10 g, 0.31 mmol) in methanol (3 ml), was added sodium methoxide (0.59 ml of 30 wt % solution in methanol, 3.1 mmol) and the reaction mixture stirred at 50° C. for 5 hours. The solution was cooled to ambient temperature, diluted with methanol (20 ml) and Amberlite IR-120(plus) resin added. (A small excess of the resin was added to obtain a solution of pH 2.5). The solution was filtered and the resin washed with methanol:water (1:1, 30 ml) and the combined filtrates concentrated under reduced pressure. The residue was purified by reverse-phase silica column chromatography using water as eluant to give the title compound as a white solid (70 mg, 71%). UV: $\nu_{max}$ (H$_2$O) 248 ($\epsilon$ 7,230), 280 ($\epsilon$ 8250)nm. $^1$H NMR: $\delta_H$ [(CD$_3$)$_2$SO] 3.38 (2H, d, J=8.35 Hz, OCH$_2$P), 3.70 (2H, m, CH$_2$), 3.95 (3H, s, OCH$_3$), 4.37 (2H, m, NOCH$_2$), 4.4–5.0 (2H, br.s, D$_2$O exchangeable PO(OH)$_2$), 6.73 (2H, br.s, D$_2$O exchangeable NH$_2$), 8.19 (1H, s H-8).

EXAMPLE 15

9-[(2-Hydroxy-2-oxo-1,4,2-dioxaphosphorinan-5-yl)methoxy]quanine

A solution of dicyclohexylcarbodiimide (0.323 g, 1.57 mmol) in t-butanol (15 ml) and DMF (2 ml) was added dropwise over 30 minutes to a solution of 9-[3-hydroxy-2-(phosphonomethoxy)propoxy]quanine (0.105 g, 0.31 mmol) and N,N-dicyclohexyl-4-morpholinocarboxamidine (0.092 g, 0.31 mmol) in 50% aqueous t-butanol (10 ml). The reaction mixture was heated under reflux for 8 hours, allowed to cool to ambient temperature overnight and then filtered. The filtrate was evaporated to dryness, water added to the residue and the mixture filtered through a glass fibre filter paper. The filtrate was evaporated to dryness and the solid obtained purified on DEAE-Sephadex (HCO$_3^-$ form) eluting with a linear gradient of aqueous triethylammonium bicarbonate (pH 7.5) from 0.050M to 0.250M. The required component was found in the 0.15M fractions. Relevant fractions were combined and evaporated to dryness co-evaporating with ethanol/water 3:1 ($\times$3) when all traces of triethylamine were removed. The residue was converted into a sodium salt form by passing an aqueous solution through a column of DOWEX 50W-X8 (Na$^+$) resin and eluting with water. Relevant fractions were combined and lyophilized to give the title compound as a white amorphous solid (58 mg) UV: $\nu_{max}$(H$_2$O) 253 ($\epsilon$ 11,600)nm. IR: $\nu_{max}$(KBr) 3408, 3140, 2956, 1696, 1611, 1529, 1479, 1382, 1323, 1239, 1210, 1176, 1082, 1044, 1012, 961, 820, 792, 777 cm$^{-1}$. $^1$H NMR: $\delta_H$[(CD$_3$)$_2$SO] 3.40 (1H, dd, J=13.1 Hz, J=3.4 Hz, OCH$_B$P), 3.54 (1H, dd, J=13.1 Hz, J=8.4 Hz, OCH$_A$P), 3.77 (1H, m, CH), 3.91 (1H, ddd, J=11.5 Hz, J=15.0 Hz, J=2.3 Hz, CHCH$_B$OP), 4.11 (1H, ddd, J=11.5 Hz, J=9.7 Hz, J=4.3 Hz, CHCH$_A$OP), 4.20 (1H, dd, J=10.6 Hz, J=3.4 Hz, NOCH$_B$), 4.29 (1H, dd, J=10.6 Hz, J=6.6 Hz, NOCH$_A$), 6.85 (2H, br.s, D$_2$O exchangeable NH$_2$), 7.90 (1H, s, H-8), 10.99 (1H, br.s, D$_2$O exchangeable NH).

EXAMPLE 16

2,6-Diamino-9-[3-hydroxy-2-(phosphonomethoxy)propoxy]purine

A solution of 9-[3-acetoxy-2-(diethoxyphosphorylmethoxy)propoxy]-6-chloro-2-formamidopurine (0.16 g, 0.33 mmol) in ethanolic ammonia (5 ml) was heated in a sealed vessel at 120° C. for 5 hours. The solution was allowed to cool to ambient temperature and the solvent was removed under reduced pressure to leave a brown residue. The residue was purified by preparative t.l.c. (dichloromethane:methanol 80:20) to give 2,6-diamino-9-[2-(diethoxyphosphorylmethoxy)-3-hydroxypropoxy]purine as a colourless gum (0.065 g). The gum (0.06 g, 0.15 mmol) was dissolved in dry DMF (1 ml) and trimethylsilyl bromide (0.3 ml, 1.53 mmol) added. After 3 hours at ambient temperature, the solvent was removed under reduced pressure and the residue obtained dissolved in 50% aqueous acetone. Evaporation of the solvent gave a solid which after crystallisation from hot water, gave the title compound as a cream solid (0.014 g, 27%). $^1$H NMR: $\delta_H$ [(CD$_3$)$_2$SO] 3.46-3.60 (2H, m, CH$_2$OH), 3.65-3.85 (3H, m, CHOCH$_2$P), 4.24 (1H, m, NOCH$_B$), 4.42 (1H, m, NOCH$_A$), 6.03 (2H, br. s, D$_2$O exchangeable NH$_2$), 6.88 (2H, br. s, D$_2$O exchangeable NH$_2$), 8.02 (1H, s, H-8), 3.3 (br.s, D$_2$O exchangeable OH, PO(OH)$_2$, water in solvent). m/z (FAB, thioglycerol matrix) 335 (MH$^+$, 6%)

EXAMPLE 17

(R)-9-3-Hydroxy-2-(phosphonomethoxy)propoxy]quanine a) To a stirred mixture of diethyl (S)-[1-(t-butyldiphenylsilyloxymethyl)-2-hydroxyethoxy]methylphosphonate (540 mg, 1.12 mmol), triphenylphosphine (440 mg, 1.68 mmol) and 2-[bis-(t-butoxycarbonyl)amino]-9-hydroxy-6-methoxypurine (prepared as described in EF-A-319228) (428 mg, 1.12 mmol) in dry THF (20 ml), cooled in ice and under a nitrogen atmosphere, was added dropwise diethyl azodicarboxylate (0.27 ml, 1.68 mmol). Within five minutes complete dissolution had occurred and the ice bath was removed. After 1 hour, the solution was evaporated to dryness and the residue obtained chromatographed on silica gel (initial eluant hexane: ethyl acetate 2:1, then hexane:ethyl acetate in the proportions 1:1, 1:2, 1:3) to yield (S)-2-[bis-(t-butoxycarbonyl)amino]-9-[3-(t-butyldiphenylsilyloxy)-2-(diethoxyphosphorylmethoxy)propoxy]-6-methoxypurine as a colourless glass (310 mg, 32%). $^1$H NMR: $\delta_H$ [(CD$_3$)$_2$SO] 0.96 (9H, s, t-Bu), 1.18, 1.19 (2$\times$3H, 2$\times$t, J=7 Hz, (OCH$_2$CH$_3$)$_2$), 1.37 (18H, br.s, 2$\times$t-Bu), 3.7-4.15 (12H, m, CHCH$_2$, (OCH$_2$CH$_3$)$_2$, OCH$_2$P, OCH$_3$), 4.45-4.70 (2H, m, NOCH$_2$), 7.25-7.75 (10H, m, 2$\times$Ph), 8.75 (1H, s, H-8). m/z: (FAB+ve ion, thioglycerol/HCl) 844 (MH$^+$, 4%), 644 (100%).

b) A solution of (S)-2-[bis-(t-butyloxycarbonyl)amino]-9-[3-(t-butyldiphenylsilyloxy)-2-(diethoxyphosphorylmethoxy)propoxy]-6-methoxypurine (300 mg, 0.36 mmol) in 67% aqueous trifluoroacetic acid (3 ml) was kept at ambient temperature for 3 hours. The solution was washed with hexane (3$\times$10 ml) and the aqueous phase evaporated to dryness. The residue obtained was chromatographed on silica gel (dichloromethane:methanol 95:5 as eluant, then 90:10) to give (R)-2-amino-9-[2-(diethoxyphosphorylmethoxy)-3-hydroxypropoxy]-6-methoxypurine as a pale yellow glass (101 mg, 70%). $^1$H NMR: $\delta_H$ [(CD$_3$)$_2$SO] 1.23 (6H, t, J=7.1 Hz, (OCH$_2$CH$_3$)$_2$), 3.5-3.65 (2H, m, CH$_2$), 3.70-3.80 (1H, m, CH), 3.96 (3H, s, OCH$_3$), 3.98-4.10 (6H, m, (OCH$_2$CH$_3$)$_2$, OCH$_2$P), 4.31 (1H, dd, J=11.27 Hz, J=6.87 Hz, NOCH$_B$), 4.45 (1H, dd, J=11.27 Hz, J=3.02 Hz, NOCH$_A$), 4.85 (1H, t, J=5.50 Hz, D$_2$O exchangeable OH), 6.60 (2H, s, D$_2$O exchangeable NH$_2$), 8.14 (1H, s, H-8). m/z: (FAB+ve ion, thioglycerol) 406 (MH$^+$, 100%).

c) To a solution of (R)-2-amino-9-[2-(diethoxyphosphorylmethoxy)-3-hydroxypropoxy)-6-methoxypurine (100 mg, 0.25 mmol) in dry dimethylformamide (1 ml) was added trimethylsilyl bromide (0.5 ml, 3.8 mmol) and the solution stirred at ambient temperature for two hours. The solvent was removed under reduced pressure and the residue co-evaporated with acetone-water, 1:1 ($\times$2). The solid obtained was crystallised from hot water to give the title compound as a cream solid (16 mg, 20%). $^1$H NMR: $\delta_H$ [(CD$_3$)$_2$SO] 3.52 (2H, m, CH$_2$OH), 3.60-3.80 (3H, m, OCH$_2$P, CH), 4.25 (1H, dd, J=11.9 Hz, J=7.1 Hz, NOCH$_B$), 4.40 (1H, dd, J=11.9 Hz, J=3.3 Hz, NOCH$_A$), 6.60 (2H, br.s, D$_2$O exchangeable NH$_2$), 8.00 (1H, s, H-8), 10.65 (1H, br.s, D$_2$O exchangeable NH), 2.6-4.1 (3H, broad, D$_2$O exchangeable OH, PO(OH)$_2$). m/z: (FAB+ve ion, thioglycerol) 336 (MH$^+$, 28%).

EXAMPLE 18

(S)-9-[(2-Hydroxy-2-oxo-1,4,2-dioxaphosphorinan-5-yl)methoxy]quanine

A solution of dicyclohexylcarbodiimide (0.615 g, 3.0 mmol) in t-butanol (15 ml) was added dropwise over 30 minutes to a solution of (R)-9-[3-hydroxy-2-(phosphonomethoxy)propoxy]quanine (0.20 g, 0.6 mmol) and N,N-dicyclohexyl-4-morpholinocarboxamidine (0.175 g, 0.6 mmol) in 50% aqueous t-butanol (30 ml). The reaction mixture was heated under reflux for 5½ hours, allowed to cool to ambient temperature and evaporated to dryness. Water was added to the residue and the resulting mixture filtered through a glass fibre filter paper. The filtrate was evaporated to dryness and the solid obtained purified on DEAE-Sephadex (HCO$_3^-$ form) eluting with a linear gradient of aqueous triethylammonium bicarbonate (pH 7.5) from 0.001M to 0.25M. Relevant fractions were combined and evaporated to dryness co-evaporating with ethanol/water 3:1 (×3) to remove all traces of triethylamine. The product was converted into the sodium salt using DOWEX 50W-X8 (Na$^+$-form). The title compound was obtained as a white powder (0.16 g, 79%) after lyphilisation.

UV: $\nu_{max}$ (H$_2$O) 253 ($\epsilon$ 11,180)nm. IR: $\nu_{max}$ (KBr) 3411, 3400, 3144, 2759, 1696, 1617, 1591, 1476, 1380, 1330, 1239, 1209, 1174, 1081, 1045, 1010, 96,, 815, 796 cm$^{-1}$. $^1$H NMR: $\delta_H$ [(CD$_3$)$_2$SO] 3.40 (1H, dd, J=12,9 Hz, J=3.3 Hz, OCH$_B$P) 3.50 (1H, dd, J=12.9 Hz, J=8 Hz, OCH$_A$P), 3.74 (1H, m, CH), 3.90 (1H, m, CH$_B$OP), 4.0–4.3 (3H, m, CH$_A$OP, NOCH$_2$), 6.75 (2H, br.s, D$_2$O exchangeable NH$_2$), 7.90 (1H, s, H-8), 10.81 (1H, br.s, D$_2$O exchangeable NH). m/z: (FAB, thioglycerol matrix) 340 (MH$^+$). [$\alpha$]$_D^{25}$ (H$_2$O) - 38.7° (c=0.93).

EXAMPLE 19

(R)-9-[3-Hydroxy-2-(phosphonomethoxy)propoxy]adenine a) To a stirred mixture of diethyl (S)-[1-(t-butyldiphenylsilyloxymethyl)-2-hydroxyethoxy]methylphosphonate (1.07 g, 2.2 mmol), triphenylphosphine (0.7 g, 2.7 mmol) and 9-hydroxy-6-phthalimidopurine (prepared as described in EP-A-319228) (0.63 g, 2.2 mmol) in dry THF (20 ml), cooled in ice and under a nitrogen atmosphere, was added dropwise diethyl azodicarboxylate (0.42 ml, 2.7 mmol). The resulting solution was stirred overnight at ambient temperature, evaporated to dryness and the residue obtained chromatographed on silica gel using hexane/ethyl acetate 3:1 as eluant. The eluant was changed as follows: hexane/ethyl acetate 1:1, hexane/ethyl acetate 1:2 and finally to ethyl acetate to give (S)-9-[3-(t-butyldiphenylsilyloxy)-2-(diethoxyphosphorylmethoxy)propoxy]-6-N-phthalimidopurine as a cream foam (1.1 g, 66%). IR: $_{max}$ (film) 3070, 2930, 2860, 1795, 1603, 1580, 1470, 1450, 1430, 1405, 1365, 1330, 1250, 1175, 1160, 1105, 1020, 970, 885, 835, 795, 780 cm$^{-1}$. $^1$H NMR: $\delta_H$ [(CD$_3$)$_2$SO] 0.97 (9H, s, t-Bu), 1.19, 1.20 (2×3H, 2×t, J=7 Hz, (OCH$_2$CH$_3$)$_2$), 3.8–4.15 (9H, m, (OCH$_2$CH$_3$)$_2$, OCH$_2$P, CHCH$_2$), 4.65 (1H, dd, J=11.5 Hz, J=6.6 Hz, NOCH$_B$), 4.78 (1H, dd, J=11.5 Hz, J=3.0 Hz, NOCH$_A$), 7.3–7.7 (10H, m, 2×Ph), 8.0–8.15 (4H, m, aromatic H), 9.04 (1H, s, H-2 or H-8), 9.08 (1H, s, H-2 or H-8). Found: C, 59.51; H, 5.76; N, 9.42%. C$_{37}$H$_{42}$N$_5$O$_8$PSi requires: C, 59.74; H, 5.69; N, 9.41%. m/z: (FAB, thioglycerol matrix) 744 (MH$^+$).

b) A solution of (S)-9-[3-(t-butyldiphenylsilyloxy)-2-(diethoxyphosphorylmethoxy)propoxy]-6-N-phthalimidopurine (0.98 g, 1.6 mmol) in dry dichloromethane (10 ml) was treated with N-methylhydrazine (0.093 ml, 1.75 mmol) at room temperature for 1 hour. The reaction mixture was filtered, the filtrate concentrated in vacuo and the residue chromatographed on silica gel using dichloromethane as the initial eluant. The eluant was changed to dichloromethane/methanol 96:4 to give (S)-9-[3-(t-butyldiphenylsilyloxy)-2-(diethoxyphosphorylmethoxy)propoxy]adenine as a colourless oil (0.61 g, 75%). UV: $\nu_{max}$ (EtOH) 260 (13,690) nm. IR: $\nu_{max}$ (film) 3322, 3176, 2930, 2902, 2857, 1643, 1594, 1471, 1427, 1405, 1398, 1325, 1292, 1251, 1112, 1051, 1026, 971, 823, 795, 741 cm$^{-1}$. $^1$H NMR: $\delta_H$ [(CD$_3$)$_2$SO] 0.94 (9H, s, t-Bu), 1.19 (2×3H, 2×t, J=7 Hz, (OCH$_2$CH$_3$)$_2$), 3.7–4.15 (9H, m, CHCH$_2$, OCH$_2$P, (OCH$_2$CH$_3$)$_2$), 4.48 (1H, dd, J=11.27 Hz, J=6 Hz, NOCH$_B$), 4.65 (1H, dd, J=11.27 Hz, J=2.75 Hz, NOCH$_A$), 7.3–7.7 (12H, m, 2×Ph+D$_2$O exchangeable NH$_2$), 8.14 (1H, s, H-2 or H-8), 8.41 (1H, s, H-2 or H-8). Found: C, 55.65; H, 6.52; N, 11.24%. C$_{29}$H$_{40}$N$_5$O$_6$PSi 0.75 H$_2$O requires: C, 55.53; H, 6.67; N, 11.16%. m/z: (FAB, thioglycerol matrix) 614 (MH$^+$).

c) (S)-9-[3-(t-Butyldiphenylsilyloxy)-2-(diethoxyphosphorylmethoxy)propoxy]adenine (0.61 g, 1 mmol) was dissolved in trifluoroacetic acid/water, 2:1 (6 ml) and the solution stirred at ambient temperature for 3 hours. Hexane (10 ml) was added and the mixture shaken. The aqueous phase was separated, washed once more with hexane (10 ml) and evaporated to dryness. The residue was treated with ethanolic ammonia solution (5 ml), at ambient temperature, for 5 minutes after which the solution was evaporated to dryness. The residue was chromatographed on silica gel using dichloromethane/methanol 90:10 as eluant to give (R)-9-[2-(diethoxyphosphorylmethoxy)-3-hydroxypropoxy]adenine as a colourless oil (0.3 g, 80%) which on prolonged standing, crystallised as white needles m.p. 98°–102°. IR: $\nu_{max}$ (film) 3340, 3210, 2995, 2930, 2910, 1660, 1645, 1600, 1470, 1445, 1415, 1395, 1370, 1330, 1300, 1240, 1210, 1165, 1125, 1045. 1020, 980, 825, 95, 735 cm$^{-1}$. $^1$H NMR: $\delta_H$ [(CD$_3$)$_2$SO] 1.23 (6H, t, J=7 Hz (OCH$_2$CH$_3$)$_2$), 3.5–3.7 (2H, m, CH$_2$OH), 3.75–3.85 (1H, m, CH), 3.95–4.15 (6H, m, (OCH$_2$CH$_3$)$_2$, OCH$_2$P), 4.38 (1H, dd, J=11.3 Hz, J=6.6 Hz, NOCH$_B$), 4.55 (1H, dd, J=11.3 Hz, J=3.0 Hz, NOCH$_A$), 4.88 (1H, t, J=5.5 Hz, D$_2$O exchangeable OH), 7.38 (2H, br.s., D$_2$O exchangeable NH$_2$), 8.15 (1H, s, H-2 or H-8), 8.43 (1H, s, H-2 or H-8). Found: C, 39.26; H, 6.05; N, 17.33%. C$_{13}$H$_{22}$N$_5$O$_6$P 1.25 H$_2$O requires: C, 39.25; H, 6.20; N, 17 61%. m/z: (FAB, thioglycerol matrix) 376 (MH$^+$).

d) To a solution of (R)-9-[2-(diethoxyphosphorylmethoxy)-3-hydroxypropoxy)adenine (0.16 g, 0.43 mmol) in dry DMF (3 ml) was added trimethylsilyl bromide (0.56 ml, 4.3 mmol) and the solution stirred at ambient temperature for 4 hours. The solvent was removed under reduced presence and the residue co-evaporated with acetone/water 1:1 (x3). The solid residue was crystallised from acetone/water (0.1 g, 77%), m.p. 200°–205°. UV: $\lambda_{max}$ (EtOH), 260 (11,800) nm. IR: $\nu_{max}$ (KBr) 3449, 3400, 3199, 3105, 2951, 2897, 1711, 1680, 1612, 1569, 1467, 1420, 1355, 1330, 1305, 1244, 1216, 1128, 1080, 924, 866 cm$^{-1}$. $^1$H NMR: $\delta_H$ [(CD$_3$)2SO]3.54 (2H, m, CH$_2$OH), 3.70–3.85 (3H, m, OCH$_2$P, CH), 4.36 (1H, dd, J=11 Hz, J=7 Hz, NOCH$_B$), 4.55 (1H, dd, J=11 Hz, J=3 Hz, NOCH$_A$), 7.51 (2H, br.s, D$_2$O exchangeable NH$_2$), 8.17 (1H, s, H-2 or H-8), 8.50 (1H, s, H-2 or H-8), 3.5–7.0 (3H, broad, PO(OH)$_2$, OH). Found: C, 32.07; H, 4.73; N, 20.46%. C$_9$H$_{14}$N$_5$O$_5$P 1 H$_2$O requires: C, 32.05; H, 4.78; N, 20.76%. m/z: (FAB, thioglycerol matrix) 320 (MH$^+$). [$\alpha$]$_D^{25}$ (0.1M NaOH)-11.5° (c=0.2).

EXAMPLE 20

(S)-9-[3-Hydroxy-2-(phosphonomethoxy)propoxy]guanine a) To a stirred solution of diethyl (R)-[2-benzyloxy-1-(hydroxymethyl)ethoxy]methylphosphonate (1.0 g, 3 mmol), triphenylphosphine (1.18 g, 4.5 mmol) and 2-[bis-(t-butoxycarbonyl)amino]-9-hydroxy-6-methoxypurine (1.15 g, 3 mmol) in dry THF (20 ml), cooled in ice and under a nitrogen atmosphere, was added, dropwise, diethyl azodicarboxylate (0.71 ml, 4.5 mmol). The resulting solution was allowed to warm to ambient temperature and left stirring for 16 hours. The solvent was evaporated under reduced pressure and the residue obtained chromatographed on silica gel using hexane/ethyl acetate 2:1 as eluant. The eluant was changed as follows: hexane/ethyl acetate 1:1, hexane/ethyl acetate 1:2 and finally to ethyl acetate to give (S)-2-[bis-(t-butoxycarbonyl)amino]-9-[3-benzyloxy-2-(diethoxyphosphorylmethoxy)propoxy]-6-methoxypurine as a colourless oil (1.85 g, 88%).

IR: $\nu_{max}$ (film) 3070, 2990, 2940, 2910, 1795, 1755, 1740, 1595, 1480, 1455, 1425, 1395, 1370, 1325, 1255, 1160, 1120, 1100, 1050, 1025, 975, 855, 795, 740, 705cm$^{-1}$. $^1$H NMR: $\delta_H$[(CD$_3$)$_2$SO] 1.20 (6H, t, J=7 Hz, (OCH$_2$CH$_3$)$_2$), 1.38 (18H, s, 2xt-Bu), 3.5–3.75 (2H, m, CH$_2$), 3.95–4.1 (7H, m, OCH$_2$P, CH, (OCH$_2$CH$_3$)2), 4.08 (3H, s, OCH$_3$), 4.45–4.65 (2H, m, NOCH$_2$) 4.51 (2H, s, OCH$_2$Ph), 7.25–7.40 (5H, m, Ph), 8.75 (1H, s, H-8). Found: C, 52.27; H, 6.77; N, 9.65%. C$_{31}$H$_{45}$N$_5$O$_{11}$P 1H$_2$O requires: C, 52.17; H, 6.77; N, 9.81%. m/z: (FAB, TDE/Na matrix) 718 (32%, M+Na+) 696 (13%, MH+).

b) Trifluoroacetic acid (2 ml) was added to an ice cooled solution of (S)-2-[bis-(t-butoxycarbonyl)amino]-9-[3-benzyloxy-2-(diethoxyphosphorylmethoxy)-propoxy]-6-methoxypurine (1.65 g, 2.3 mmol) in dry dichloromethane (30 ml) an the resulting solution left for 2 hours. After warming to ambient temperature, 10% Pd-C (800 mg) was added and the mixture hydrogenated at ambient temperature and pressure for 2 hours. The reaction mixture was filtered, the catalyst washed with dichloromethane (20 ml), the filtrate washed with saturated aqueous sodium bicarbonate solution, brine, dried (MgSO$_4$) and evaporated to leave a colourless viscous oil. Chromatography of the oil on silica gel using dichloromethane/methanol 95:5 as the initial eluant, then changing the eluant to dichloromethane/methanol 90:10 gave (S)-2-amino-9-[2-(diethoxyphosphorylmethoxy)-3-hydroxypropoxy]-6-methoxypurine as a colourless oil (0.65 g, 67%). IR: $\nu_{max}$ (film) 3360, 3230, 2990, 2940, 2910, 1620, 1585, 1500, 1485, 1455, 1390, 1335, 1265, 1240, 1165, 1120, 1060, 1025, 975, 825, 785cm$^{-1}$. $^1$H NMR: $\delta_H$ [(CD$_3$)$_2$SO] 1.23 (6H, t, J=7 Hz, (OCH$_2$CH$_3$)$_2$), 3.45–3.60 (2H, m, collapses to d on D$_2$O exchange, CH$_2$OH), 3.70–3.85 (1H, m, CH), 3.96 (3H, s, OCH$_3$), 3.9–4.15 (6H, m, (OCH$_2$CH$_3$, OCH$_2$P), 4.31 (1H, dd, J=11.3 Hz, J=6.9 Hz, NOCH$_B$), 4.45 (1H, dd, J =11.3 Hz, J=3 Hz, NOCH$_A$), 4.84 (1H, t, J=5.5 Hz, D$_2$O exchangeable OH), 6.59 (2H, br.s, D$_2$O exchangeable NH$_2$), 8.14 (3H, s, H-8). m/z: (FAB, thioglycerol matrix) 406 (MH+).

c) To a solution of (S)-2-amino-9-[2-(diethoxyphosphorylmethoxy)-3-hydroxypropoxy]-6-methoxypurine (0.56 g, 1.38 mmol) in dry dimethylformamide (5 ml) was added trimethylsilyl bromide (1.82 ml, 13.8 mmol) and the solution stirred at ambient temperature for 3 hours. The solvent was removed under reduced pressure and the residue co-evaporated with acetone/water 1:1 (x2). The white solid obtained was crystallised from hot water to give the title compound as a white solid (0.305 g, 66%). IR:$\nu_{max}$ (KBr) 3380, 3320, 3160, 1715, 1645, 1600, 1385, 1185, 1160, 1100, 1060, 1045, 925, 770 cm$^{-1}$. $^1$H NMR: $\delta_H$(D$_2$O+NH$_3$) 3.61 (1H, dd, J=12.1 Hz J=9.9 Hz, CH$_B$P), 3.65–3.75 (2H, m, CH$_A$P, CH$_B$OH), 3.82–3.89 (1H, m, CH), 3.93 (1H, dd, J=12.3 Hz, J=3.6 Hz, CH$_A$OH), 4.46–4.53 (2H, m, NOCH$_2$), 8.03 (1H, s, H-8). Found: C, 32.24; H, 4.16; N, 20.59%. C$_9$H$_{14}$N$_5$O$_7$P requires: C, 32.24; H, 4.21; N, 20.89%.

m/z: (FAB, thioglycerol matrix) 336 (MH+). [α]$_D^{25}$ (0.1M NaOH)+12.8° (c=0.43).

EXAMPLE 21

(R)-9-[(2-Hydroxy-2-oxo-1,4,2-dioxaphosphorinan-5-yl)methoxy]guanine

A solution of dicyclohexylcarbodiimide (0.615 g, 3.0 mmol) in t-butanol (10 ml) was added dropwise over 30 minutes to a solution of (S)-9-[3-hydroxy-2-(phosphonomethoxy)propoxy]guanine (0.20 g, 0.6 mmol) and N,N-dicyclohexyl-4-morpholinocarboxamidine (0.175 g, 0.6 mmol) in 50% aqueous t-butanol (30 ml). The reaction mixture was heated under reflux for 4 hours, allowed to cool to ambient temperature and evaporated to dryness. Water was added to the residue and the mixture filtered through a glass fibre filter paper. The filtrate was evaporated to dryness and the solid obtained purified on DEAE-Sephadex (HCO$_3$− form) eluting with a linear gradient of aqueous triethylammonium bicarbonate (pH 7.5) from 0.001M to 0.25M. Relevant fractions were combined and evaporated to dryness co-evaporating with ethanol/water, 3:1 (x2) to remove all traces of triethylamine. The product was converted into the sodium salt using DOWEX 50W-X8 (Na+ form). The title compound was obtained as a white solid (0.12 g, 59%) after lyophilisation. IR: $\nu_{max}$ (KBr) 3400, 3140, 1690, 1610, 1475, 1380, 1240, 1208, 1079, 1040, 1010, 960, 790 cm$^{-1}$. $^1$H NMR: $\delta_H$ [(CD$_3$)$_2$SO] 3.42 (1H, dd, J=13.2 Hz, J=3.3 Hz, OCH$_B$P), 3.55 (1H, dd, J=13.2 Hz, J=8 Hz, OCHAP), 3.79 (1H, m, CH), 3.92 (1H, m, CH$_B$OP), 4.07–4.32 (3H, m, CH$_A$OP, NOCH$_2$), 6.86 (2H, br.s, D$_2$O exchangeable NH$_2$), 7.90 (1H, s, H-8), 10.97 (1H, br.s, D$_2$O exchangeable NH). m/z: (FAB, thioglycerol) 318 (M-Na+2H+), 340 (MH+).

EXAMPLE 22

(S)-9-[3-Hydroxy-2-(phosphonomethoxy)propoxy]adenine a) To a stirred solution of diethyl (R)-[2-benzyloxy-1-(hydroxymethyl)ethoxy]methylphosphonate (0.9 g, 2.7 mmol), triphenylphosphine (1.06 g, 4 mmol) and 9-hydroxy-6-N-phthalimidopurine (0.76 g, 2.7 mmol) (prepared as in EP-A-319228) in dry THF (15 ml), cooled in ice and under a nitrogen atmosphere, was added, dropwise, diethyl azodicarboxylate (0.6 ml, 4 mmol). The resulting solution was allowed to warm to ambient temperature and stirred for 4 hours. The solvent was evaporated under reduced pressure and the residue obtained chromatographed on silica gel using hexane/ethyl acetate 1:1 as the initial eluant. The eluant was changed to ethyl acetate to give (S)-9-[3-benzyloxy-2-(diethoxyphosphorylmethoxy)propoxy]-6-N-phthalimidopurine as a pale brown oil (1.16 g, 72%) which was used directly in the next stage.

b) A solution of (S)-9-[3-benzyloxy-2-(diethoxyphosphorylmethoxy)propoxy]-6-N-phthalimidopurine (0.83 g, 1.39 mmol) in dry dichloromethane (10 ml) was treated with N-methylhydrazine (0.08 ml, 1.53 mmol) at ambient temperature for 3 hours. The reaction mixture was filtered, the filtrate concentrated in vacuo and the residue chromatographed on silica gel using dichloromethane/methanol 98:2 as eluant to give (S)-9-[3-benzyloxy-2-(diethoxyphosphorylmethoxy)propoxy]adenine as a colourless gum (0.27 g, 41%). IR: $\nu_{max}$ (film) 3320, 3180, 2990, 2905, 1650, 1595, 1470, 1455, 1410, 1390, 1370, 1295, 1245, 1160, 1095, 1050, 1025, 970, 820, 790, 730, 700 cm$^{-1}$. $^1$H NMR: $\delta_H$ [(CD$_3$)$_2$SO] 1.21 (2x3H, 2xt, J=7 Hz, (OCH$_2$CH$_3$)$_2$), 3.61-3.72 (2H, m, CH$_2$OCH$_2$Ph), 3.96-4.12 (7H, m, CH, OCH$_2$P, (OCH$_2$CH$_3$)$_2$), 4.40-4.58 (2H, m, NOCH$_2$), 4.52 (2H, s, OCH$_2$Ph), 7.25-7.50 (7H, m, Ph+D$_2$O exchangeable NH$_2$), 8.15 (1H, s, H-2 or H-8), 8.41 (1H, s, H-2 or H-8).

c) 10% Pd-C (50 mg) was added to a solution of (S)-9-[3-benzyloxy-2-(diethoxyphosphorylmethoxy)-propoxy]adenine (0.21 g, 0.45 mmol) in dichloromethane (5 ml) and trifluoroacetic acid (1ml) and the mixture hydrogenated at atmospheric pressure and ambient temperature for 5 hours. The mixture was filtered, the filtrate evaporated and the residue obtained dissolved in ethanolic ammonia solution (5 ml). After 15 minutes the solvent was evaporated and the residue chromatographed on silica gel using dichloromethane/methanol 90:10 as eluant. T.l.c. examination of the product indicated traces of a non UV absorbing impurity which was removed by prep. t.l.c. using dichloromethane/methanol 88:12 as eluant. (S)-9-[2-(diethoxyphosphorylmethoxy)3-hydroxypropoxy]adenine was obtained as a colourless gum (0.11 g, 65%). $^1$H NMR: $\delta_H$[(CD$_3$)$_2$SO] 1.23 (6H, t, J=7 Hz, (OCH$_2$CH$_3$)$_2$), 3.5-3.65 (2H, m, CH$_2$OH), 3.75-3.85 (1H, m, CH), 3.98-4.15 (6H, m, OCH$_2$P, (OCH$_2$CH$_3$)$_2$), 4.38 (1H, dd, J=6.6 Hz, J=11.3 Hz, NOCH$_B$), 4.54 (1H, dd, J=3 Hz, J=11.3 Hz, NOCH$_A$), 4.88 (1H, t, J=5.5 Hz, D$_2$O exchangeable OH), 7.38 (2H, br.s, D$_2$O exchangeable NH$_2$), 8.15 (1H, s, H-2 or H-8), 8.43 (1H, s, H-2 or H-8). m/z: (FAB+, thioglycerol matrix) 376 (MH+).

d) To a solution of (S)-9-[2-(diethoxyphosphorylmethoxy)-3-hydroxypropoxy]adenine (0.09 g, 0.24 mmol) in dry dichloromethane (3 ml) was added trimethylsilyl bromide (0.31 ml, 2.4 mmol) and the solution stirred at ambient temperature for 4 hours. The solvent was removed under reduced pressure and the residue co-evaporated with acetone/water 1:1 (x3). Crystallisation of the residue from water/acetone gave the title compound as a white solid (0.06 g, 78%), mp. 93°-198° C.
$^1$H NMR: $\delta_H$ [(CD$_3$)$_2$SO] 3.55 (2H, m, CH$_2$OH), 3.65-3.85 (3H, m, OCH$_2$P, CH), 4.36 (1H, dd, J=7 Hz, J=11 Hz, NOCH$_B$), 4.55 (1H, dd, J=3 Hz, J=11 Hz, NOCH$_A$), 7.61 (2H, br.s, D$_2$O exchangeable NH$_2$), 8.19 (1H, s, H-2 or H-8), 8.52 (1H, s, H-2 or H-8), 2.7-5.5 (3H, broad, D$_2$O exchangeable PO(OH)$_2$, OH).

Antiviral Activity

1. Plaque Reduction Test for Herpes Simplex Viruses 1 and 2

Vero or MRC-5 cells were grown to confluence in 24 well multi-dishes (well diameter=1.5 cm). The drained cell monolayers were each infected with approximately 50 infectious particles of herpes simplex virus 1 (HSV-1; HFEM strain) or herpes simplex virus 2 (HSV-2; strain MS) in 100 μl of phosphate-buffered saline. The virus was adsorbed for 1 hour at room temperature. After adsorption, residual inoculum was removed from each well and replaced with 0.5 ml of Eagle's MEM containing 5% newborn calf serum and 0.9% agarose (A37). Once the agarose had set, dilutions of the test compound, which had been prepared in Eagle's MEM (containing 5% newborn calf serum), were added, each well receiving 0.5 ml of liquid overlay. The test compound was diluted to give the following series of concentrations: 200, 60, 20, 6 ... 0.06 μg/ml; final concentrations in the assay ranged, therefore, between 100μg/ml and 0.03μg/ml. The infected cultures were incubated at 37° C. in a uumidified atmosphere of 5% CO$_2$ until plaques were clearly visible (2 or 3 days for Vero cells, usually 1 day for MRC-5 cells).

2. Plaque Reduction Test for Varicella Zoster Virus

MRC-5 cells were grown to confluence in 24 well multi-dishes (well diameter=1.5cm). The drained cell monolayers were each infected with approximately 50 infectious particles of varicella zoster virus (VZV; Ellen strain) in 100 μl of phosphate-buffered saline. The virus was adsorbed for 1 hour at room temperature. After adsorption, residual inoculum was removed from each well and replaced with 0.5 ml of Eagle's MEM containing 5% heat-inactivated foetal calf serum and 0.9% agarose (A37). Once the agarose had set, dilutions of the test compound, which had been prepared in Eagle's MEM (containing 5% heat-inactivated foetal calf serum), were added, each well receiving 0.5 ml of liquid overlay. The test compound was diluted to give the following series of concentrations: 200, 60, 20, 6. ..0.06 μg/ml; final concentrations in the assay ranged, therefore, between 100 μg/ml and 0.03 μg/ml. The infected cultures were incubated at 37° C. in a humidified atmosphere of 5% CO$_2$ until plaques were clearly visible (5 or 6 days).

Cultures from 1 and 2 were fixed in formal saline, the agarose overlays were carefully washed off, and then the cell monolayers were stained with carbol fuchsin. A stereo microscope wasused to count plaques. The IC$_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occurred was recorded.

3. CPE Inhibition Test (Established Monolayer) for Lentiviruses $3 \times 10^4$ sheep choroid plexus (SCP) cells were plated into individual wells of a 96 well microtitre plate in 100 μl of Eagle's MEM with Hanks' salts containing 10% heat inactivated foetal calf serum (FCS). When monolayers had become established (after 1 or 2 days growth) they were washed with 200 μl of maintenance medium (Eagle's MEM with Hanks'salts containing 0.5% FCS) and infected with 100 μl of visna virus (strain K184) in maintenance medium (20 TCID$_{50}$/ml). Test samples were diluted with maintenance medium in further 96 well microtitre plates over the range 200-0.06 μg/ml by 3-fold dilution steps. 100 μl of the diluted samples was then transferred directly onto virus-infected monolayers (final concentration range therefore 100-0.03 μg/ml) and incubated at 37° C. in a humidified atmosphere containing, 5% CO$_2$ until virus-induced CPE was maximal in the untreated virus-infected controls (usually 12-14 days). The plates were fixed with formal saline and stained with crystal violet. Virus-induced CPE was then scored microscopically and the minimum concentration of sample giving complete protection of the cell monolayers (MIC) determined.

4. Plaque Reduction Test for Cytomegalovirus

MRC-5 cells were grown to confluence in 24 well multi-dishes (well diameter=1.5 cm). The drained cell monolayers were each infected with approximately 50 infectious particles of cytomegalovirus (CMV; AD-169 strain) in 100 μl of phosphate-buffered saline. The virus wasadsorbed for 1 hour at room temperature. After adsorption, residual inoculum was removed from each well and replaced with 1 ml of Eagle's MEM containing 10% heatinactivated foetal calf serum and 0.9% agarose (A37). Once the agarose had set, dilutions of the test compound, which had been prepared in Eagle's MEM (containing 10% heat-inactivated calf serum), were added, each well receiving 1 ml of liquid overlay. The test compound was diluted to give the following series of concentrations: 200, 60, 20, 6 . . . 0.06 μg/ml; final concentrations in the assay range, therefore, between 100 μg/ml and 0.03 μg/ml. The infected cultures were incubated at 37° C. in a humidified atmosphere containing 55 $CO_2$ until plaques were clearly visible (about 12 days). The cultures are fixed in formol saline, the agarose overlays were carefully washed off, and then the cell monolayers were stained with carbol fuchsin. A stereo microscope was used to count plaques. The $IC_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occurs was recorded.

5. Test for Human Immunodeficiency Virus (HIV)

a) Cell cytotoxicity test

Peripheral human lymphocytes were isolated by density gradient centrifugation from blood donations of healthy volunteers. The 'buffy coat' fractions of these donations were provided by blood donation centres.

The buffy coat was diluted 1:1 with sterile phosphate buffered saline (PBS; 50 mM sodium phosphate, pH 7.4, 0,9% sodium chloride) and subsequently layered over Ficoll. Following centrifugation (30 minutes at 400 x g) the supernatant was discarded and the interphase containing the lymphocytes was recovered. The lymphocytes were washed two times in PBS and were resuspended finally in cell culture medium.

A viability staining was performed by means of the trypan blue dye-exclusion method. The concentration of cells in the suspension and the percentage of viable cells were calculated. Subsequently, the cell suspension was adjusted to a concentration of $1 \times 10^7$ cells/ml. This cell suspension was transferred to tissue culture flasks: Two thirds of the cell suspension were polyclonally activated by addition of phytohemagglutinin (final concentration 5 μg.ml). One third of the cell suspension remained unstimulated.

The lymphocytes were cultivated in an incubator with a humidified atmosphere and 5% $CO_2$ for 48 to 64 hours at 37° C. Following this incubation period, cells were harvested by centrifugation, resuspended in cell culture medium and counted. Stimulated and unstimulated cells were combined in a ratio of 2:1 and adjusted to a concentration of $2 \times 10^6$ cells/ml with cell culture medium that contained, in addition, 10 units/ml of human recombinant interleukin-2.

Only those preparations of lymphocytes were employed for the screening test in which more than 70% of the stimulated lymphocytes expressed the CD 25 antigen and more than 45% of the lymphocytes expressed the CD 4 antigen.

100 μg of this lymphocyte suspension was added to each well of microtiter plates containing the test compounds serially diluted over the range 100 μM to 0.1 μM. Subsequently, the microtiter plates were cultivated for 4 days at 37° C.

Survival and proliferation of the lymphocytes grown in the presence of the compound were measured by a quantitative colorimetric assay. Viable cells cultivated in the presence of the dye MTT [3-4,5-dimethylthiazol-2-yl)-3,5-diphenyltetrazolium) reduce this pale yellow substrate by activity of their mitochondrial dehydrogenases to a purple formazan. The amount of product which is a function of cell number and metabolic cellular activity was quantified photometrically. By this assay, potential cytotoxic and cytostatic effects of compounds towards lymphocytes were detected precisely.

Microtiter plates were centrifuged for 5 minutes at $900 \times g$. The supernatant was discarded and the cells of each well were resuspended in 50 μl of cell culture medium containing 2 mg/ml of MTT. After four hours of incubation at 37° C. 100 μl of solvent (isopropanol with 0.04 N HCl and 10% (v/v) Triton 100) was added to each well. By shaking the microtiter plates the formazan was solubilized. Subsequently, the plates were evaluated in an ELISA photometer in the dual wavelength mode (measuring wavelength: 550 nm; reference wavelength: 690 nm).

For each well the difference in absorption (abs. 550 nm - abs. 690 nm) was calculated. These data provided the basis for further evaluation of the cytotoxicity test. The approximate $CD_{50}$ (halfmaximal cytotoxic dose) of each compound was calculated.

b) HIV Suppression test

Peripheral human lymphocytes were prepared, cultivated, and harvested as above. Following the determination of the lymphocyte surface markers, unstimulated and mitogen stimulated cells were combined in a ratio of 1:2.

Under safety conditions these cells are infected with a standard preparation of HIV. The cells are sedimented by centrifugation. The supernatant was discarded and cells were resuspended in the HIV inoculum.

This inoculum is a liquid suspension of HIV-1 strain virus, pretested and adjusted to a titer that results in a synthesis of viral core protein p24 of > 100 ng/ml at day four following infection of human lymphocytes according to the protocol.

$3 \times 10^8$ lymphocytes were resuspended in 1 ml HIV inoculum and incubated at 37° C. for 60 minutes. Subsequently, the cells were washed two times with 50 ml of culture medium and resuspended in culture medium containing 10 units/ml of human recombinant interleukin-2 to yield a cell concentration of $2 \times 10^6$ cells/ml. 100 μl of this cell suspension was added to each well of the microtiter plates containing the diluted solutions of the compounds. The microtiter plates were cultivated in an incubator with a humidified atmosphere and 5% $CO_2$ at 37° C.

Accordingly, a fraction of lymphocytes was mock-infected with the same virus preparation that was heat inactivated (30 minutes at 56° C.) prior to infection.

On each of the days 2,3 and 4 post infection one of the microtiter plates which had been established in triplicate was prepared for determination of viral replication. Viral RNA is determined within the cells whereas the viral core protein p24 was detected in the supernatant of the lymphocyte culture.

Accordingly, 150 μl of supernatant were removed from each well and transferred to the well of a microtiter plate containing 50 μl well of SDS (sodium dodecylsulfate, 0.08%). These plates were stored frozen. 50 μl of stop solution (1% SDS, 20 mM sodium acetate, pH 5.0, and 200 μg/ml heparin) were added to the cells remaining in each well. The plates were stored frozen.

The concentration of p24 synthesized by the HIV infected cells was determined by means of a sandwich ELISA, while the concentration of viral RNA was quantitated by nucleic acid hybridisation, using a $^{32}P$-labelled DNA probe for the gag/pol region of the viral genome. Absolute levels of viral antigen and RNA in drug treated samples were compared with untreated, virus-infected controls and the percentage inhibition calculated.

Results

| | $IC_{50}$ (µg/ml) | | | MIC (µg/ml) |
|---|---|---|---|---|
| | Herpes Simplex virus | | Varicella | Visna |
| Example No. | Type 1 HFEM strain in Vero cells | Type 2 MS strain in MRC-5 cells | Zoster virus Ellen strain in MRC-5 cells | Virus K184 strain in SCP cells |
| 1 | >100 | >100 | >100 | 100 |
| 2 | >100 | 69 | 80 | 3 |
| 3 | >100 | >100 | 51 | 10 |
| 4 | 1.1 | 0.08 | 0.06 | <0.003 |
| 5 | 59 | — | <3 | — |
| 6 | >100 | >100 | 66 | 0.3 |
| 8 | >100 | >100 | 60 | 1 |
| 10 | 17 | 7.3 | 21 | <0.003 |
| 11 | >100 | — | >100 | 30 |
| 12 | 24 | — | <3 | 0.3 |
| 13 | 3.7 | — | 0.5 | <0.03 |
| 14 | <3 | — | <0.03 | <0.03 |
| 15 | 29 | — | <3 | — |
| 17 | 7 | 10 | 17 | |
| 18 | 21 | 15 | 13 | |
| 20 | 25 | 23 | 52 | |
| 21 | 73 | 36 | 24 | |

At concentrations up to 30 µg/ml, none of the compounds were cytotoxic for the cell monolayers used in any of the above the tests.

Against CMV virus, the compounds of Examples 17, 18, 20 and 21 gave $IC_{50}$ values of 3, 3, 29 and 17 µg/ml respectively.

Against HIV virus, the following results were obtained.

| | | % Inhibition on Days 3 and 4 after infection | | | |
|---|---|---|---|---|---|
| | | Viral Antigen | | Viral RNA | |
| Ex. No. | Concn. (µM) | Day 3 | Day 4 | Day 3 | Day 4 |
| 2 | 10 | 89 | 91 | 87 | 93 |
| 4 | 10 | 100 | 99 | 99 | 95 |
| 7 | 10 | 95 | 77 | 95 | 64 |
| 10 | 1 | 11 | 44 | 17 | 53 |
| 12 | 10 | 77 | 100 | 47 | 100 |
| 13 | 10 | 99 | 100 | 96 | 97 |
| 14 | 10 | 100 | 100 | 100 | 99 |
| 15 | 1 | 100 | 52 | 72 | 65 |
| 17 | 1 | 100 | 35 | 73 | 54 |
| 18 | 10 | 100 | 33 | 92 | 32 |
| 19 | 10 | 80 | 91 | 83 | 90 |
| 20 | 1 | 54 | 15 | 10 | 14 |
| 21 | 10 | 50 | 7 | 64 | 0 |

We claim:

1. A compound of formula (I), or a pharmaceutically acceptable salt thereof:

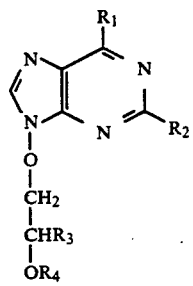

wherein $R_1$ is hydroxy, amino, chloro or $OR_7$ wherein
$R_7$ is $C_{1-6}$ alkyl, phenyl or phenyl $C_{1-2}$ alkyl either of which phenyl moieties may be substituted by one or two subststituents selected from halo, $C_{1-4}$ alkyl or $C_{1-4}$ alkoxy;

$R_2$ is amino or, when $R_1$ is hydroxy or amino, $R_2$ may also be hydrogen;

$R_3$ is hydrogen, hydroxymethyl or acyloxymethyl wherein the acyl moiety os $C_{1-7}$ alkanoyl or optionally substituted benzoyl;

$R_4$ is a group of formula:

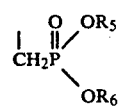

wherein $R_5$ and $R_6$ are independently selected from hydrogen, $C_{1-6}$ alkyl and optionally substituted phenyl; or
$R_3$ and $R_4$ together are:

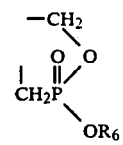

wherein
$R_6$ is as defined above; and
wherein the optional substituents for the phenyl or benzoyl are 1-3 groups or atoms selected from halogen, $C_{1-4}$ alkyl, and $C_{1-4}$ alkoxy.

2. A compound according to claim 1 wherein $R_1$ is hydroxy and $R_2$ is amino.

3. A compound according to claim 1 wherein $R_1$ is amino and $R_2$ is hydrogen.

4. A compound according to claim 1 wherein $R_3$ is hydroxymethyl.

5. A compound according to claim 1 wherein $R_5$ and $R_6$ are both hydrogen.

6. A compound selected from the group consisting of:
9-[2-(diethoxyphosphorylmethoxy)ethoxy]adenine,
9-[2-(phosphonomethoxy)ethoxy]adenine,
9-[2-(diethoxyphosphorylmethoxy)ethoxy]guanine,
9-[2-(phosphonomethoxy)ethoxy]guanine,
9-[2-[ethoxy(hydroxy)phosphorylmethoxy)ethoxy]-guanine,
9-[2-(diethoxyphosphorylmethoxy)-3-hydroxy-propoxy]adenine,
9-[3-hydroxy-2-(phosphonomethoxy)propoxy]adenine, 9-[2-[ethoxy(hydroxy)phosphorylmethoxy]-3-hydroxypropoxy]adenine,
9-[2-(diethoxyphosphorylmethoxy)-3-hydroxypropoxy]-guanine,
9-[3-hydroxy-2-(phosphonomethoxy)propoxy]guanine,
2,6-diamino-9-[2-(diethoxyphosphorylmethoxy)-ethoxy]purine,
2,6-diamino-9-[2-phosphonomethoxy)ethoxy]purine,
2-amino-6-chloro-9-[2-(phosphonomethoxy)ethoxy]-purine,
2-amino-6-methoxy-9-[2-(phosphonomethoxy)ethoxy]purine,
9-[(2-hydroxy-2-oxo-1,4,2-dioxaphosphorinan-5-yl)-methoxy]guanine,
2,6-diamino-9-[3-hydroxy-2-(phosphonomethoxy)-propoxy]purine,
(R)-9-[3-hydroxy-2-(phosphonomethoxy)propoxy]-guanine,
(S)-9-[(2-hydroxy-2-oxo-1,4,2-dioxaphosphorinan-5-yl)-methoxy]guanine,
(R)-9-[3-hydroxy-2-(phosphonomethoxy)propoxy]adenine,
(S)-9-[3-hydroxy-2-(phosphonomethoxy)propoxy]-guanine,
(R)-9-[(2-hydroxy-2-oxo-1,4,2-dioxaphorphorinan-5-yl)methoxy]guanine, and
(S)-9-[3-hydroxy-2-(phosphonomethoxy)propoxy]adenine.

7. A compound according to claim 1, wherein $R_3$ is hydrogen.

8. The compound 9-[2-phosphonomethoxyethoxy]adenine.

* * * * *